US005629971A

United States Patent [19]
Jones et al.

[11] Patent Number: 5,629,971
[45] Date of Patent: May 13, 1997

[54] SCAN SPEED FOR TRANSMISSION EXPOSURE REDUCTION IN A NUCLEAR MEDICINE CAMERA

[75] Inventors: Steven M. Jones, Pleasanton; Michael J. Janicki, San Jose; Thomas F. Lang, Fremont; John R. Liebig, San Jose; Xiaohan Wang, Alameda, all of Calif.

[73] Assignee: ADAC Laboratories, Milpitas, Calif.

[21] Appl. No.: 439,111

[22] Filed: May 11, 1995

[51] Int. Cl.$^6$ .................................................. G21K 5/10
[52] U.S. Cl. .................... 378/145; 378/146; 250/363.04
[58] Field of Search ................................. 378/146, 108, 378/109, 110, 111, 112, 145, 4; 250/363.04

[56] References Cited

U.S. PATENT DOCUMENTS

| | | | |
|---|---|---|---|
| 5,379,333 | 1/1995 | Toth | 378/16 |
| 5,400,378 | 3/1995 | Toth | 378/16 |
| 5,450,462 | 9/1995 | Toth et al. | 378/16 |

OTHER PUBLICATIONS

Patrick Tan, et al., *A scanning Line Source for Simultaneous Emission* . . . , The Journal of Nuclear Medicine, Oct., 1993, pp., 1752–1758.

R. J. Jaszczak, et al., *Fast Transmission CT for Determining Attenuation Maps* . . . , The Journal of Nuclear Medicine, Sep., 1993, pp. 1577–1586.

Eric C. Frey, et al., *Simultaneous Acquisition of Emission and Transmission Data* . . . , The Journal of Nuclear Medicine, Dec., 1992, pp. 2238–2245.

C. H. Tung, et al. *Non-Uniform Attenuation Correction Using Simultaneous Transmission and Emission* . . . , 0–70813–0513–2/92, pp. 2018–2022.

S. H. Manglos, *Truncation artifact suppression in cone-beam radionuclide* . . . , Phys. Med. Biol., 1992, pp. 549–562.

C.H. Tung, G.T. Gullberg, G.L. Zeng, P.E. Christian, F.L. Datz, H.T. Morgan, "Non-Uniform Attenuation Correction Using Simultaneous Transmission and Emission Converging Tomography", IEEE, pp. 2018–2022.

*Primary Examiner*—Don Wong
*Attorney, Agent, or Firm*—Blakely, Sokoloff, Taylor & Zafman LLP

[57] ABSTRACT

A scan speed procedure and method wherein a minimum radiation exposure period is determined on an object by object basis for a transmission study. Two transmission scans are performed including a prescan followed by a second transmission scan phase. The first transmission prescan is performed using a radiation source over the object. This prescan is of a rapid and predetermined duration (Tp). A resultant count density associated with the object is then generated and examined. The portion having the smallest count density (Cm) is determined and a value (Co) representing the minimum required number of counts for transmission study is given. From the above, a transmission period (Ts) is determined by the system and the second transmission scan phase is performed for the duration Ts using a multi-pass scan phase. The computed duration Ts represents the minimum exposure duration required to collect transmission data to ensure that the count density distribution associated with the object will contain at least Cm count density over each portion of the object.

24 Claims, 23 Drawing Sheets

FIG_1

FIG_2

FIG_3

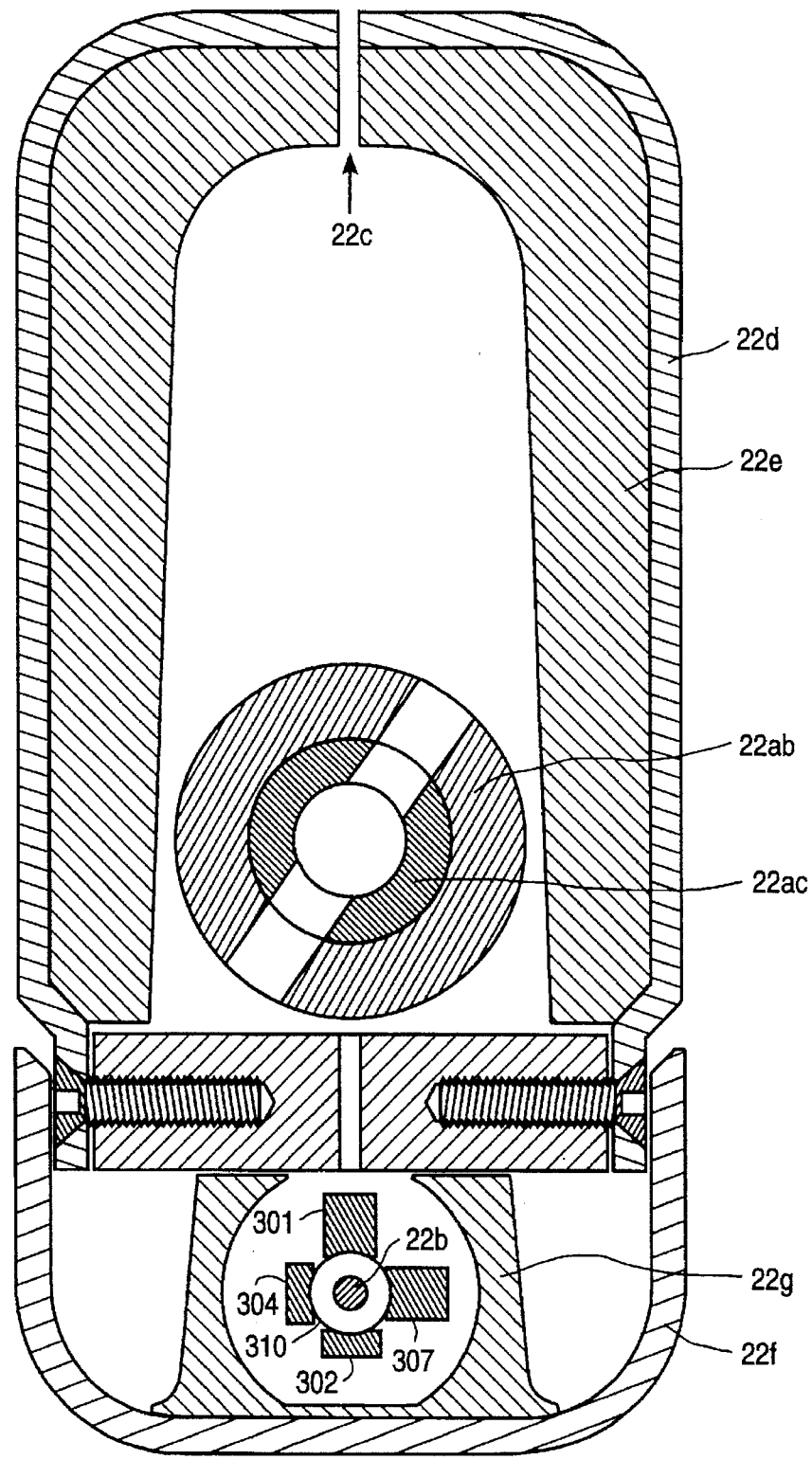
FIG_8C

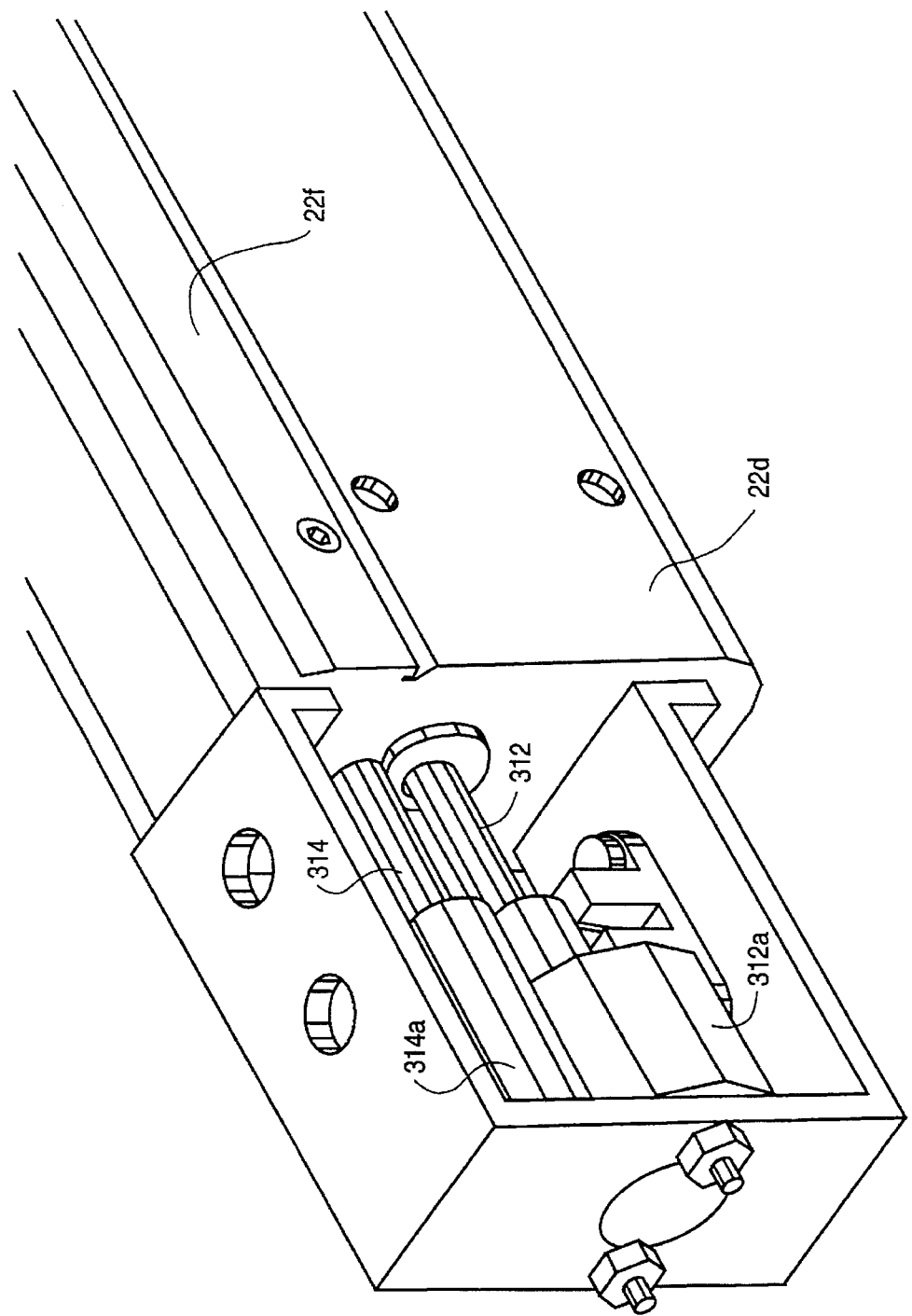

```
                    ┌─────────┐
                    │  ENTER  │
350                 │   352   │
                    └────┬────┘
                         ▼
              ┌────────────────────┐
              │ DETERMINE SHAPE OF │
              │OBJECT TO ARRIVE AT │
              │    BODY CONTOUR    │
              │         354        │
              └──────────┬─────────┘
                         ▼
              ┌────────────────────┐
              │   GIVEN AN ANGLE   │
              │     OF ROTATION    │
              │  CALCULATE THE     │
              │UNOBSTRUCTED PORTIONS│
              │ OF THE DETECTOR'S  │
              │   FIELD OF VIEW    │
              │         356        │
              └──────────┬─────────┘
                         ▼
              ┌────────────────────┐
              │SELECT PROPER FILTER│
              │ FOR MINIMIZING     │
              │  COUNT DENSITY     │
              │    THROUGH THE     │
              │UNOBSTRUCTED PORTIONS│
              │ OF THE DETECTOR'S  │
   ┌────────┐ │FIELD OF VIEW   358 │
   │POSITION│ └──────────┬─────────┘
   │DETECTOR│            ▼
   │TO NEXT │ ┌────────────────────┐
   │ANGLE OF│ │INSTALL THE PROPER  │
   │ROTATION│ │FILTER IN LINE      │
   │   366  │ │SOURCE ASSEMBLY  360│
   └────▲───┘ └──────────┬─────────┘
        │                ▼
        │     ┌────────────────────┐
        │     │PERFORM TRANSMISSION│
        │     │SESSION AT ANGLE OF │
        │     │   ROTATION     362 │
        │     └──────────┬─────────┘
        │                ▼
        │         ╱─────────╲
        │  YES   ╱ NEXT ANGLE?╲
        └───────◁    364      ▷
                 ╲           ╱
                  ╲─────────╱
                       │NO
                       ▼
                  ┌─────────┐
                  │ RETURN  │
                  │   368   │
                  └─────────┘
```

FIG_9

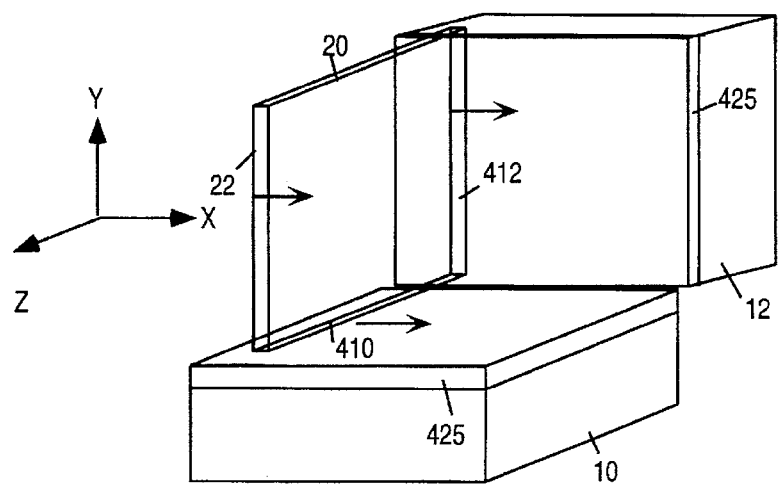
FIG_10A
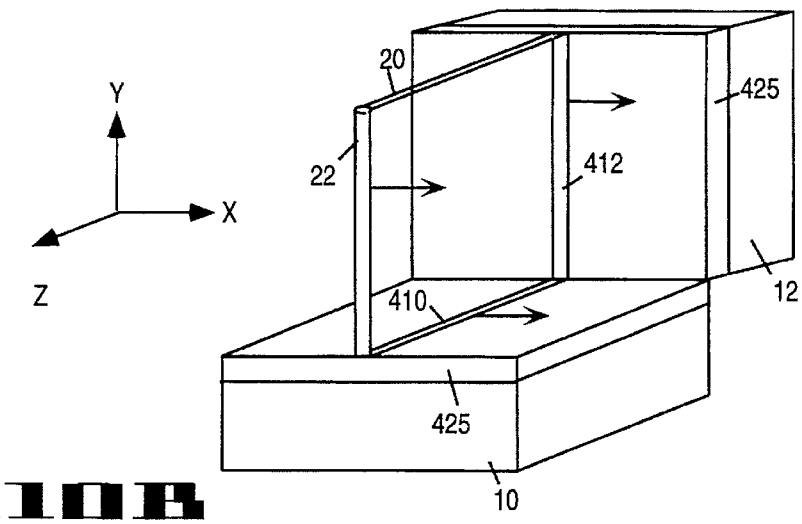
FIG_10B
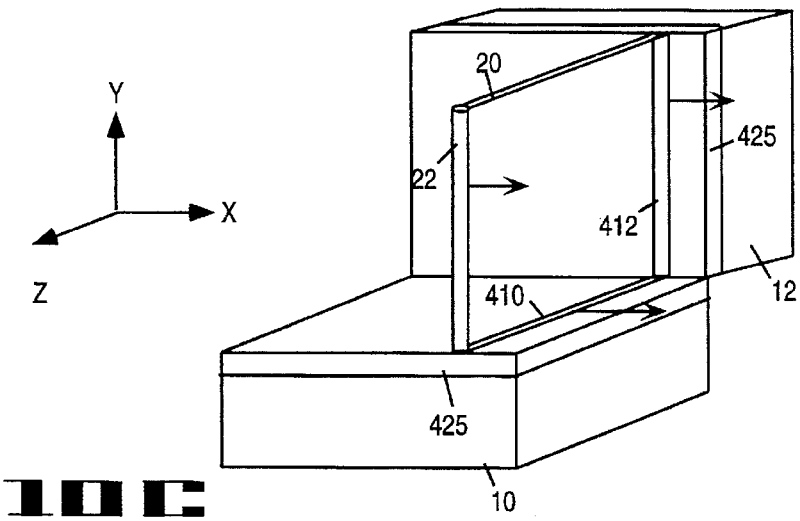
FIG_10C

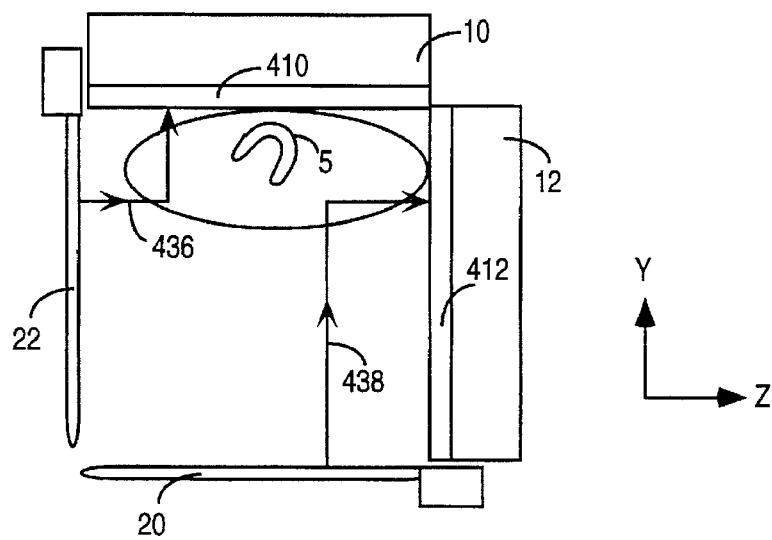
FIG_11A
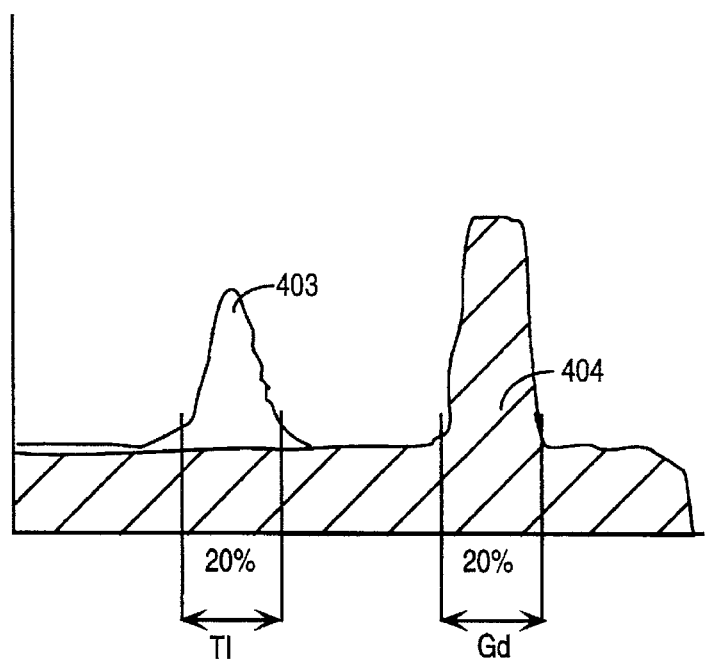
FIG_11B

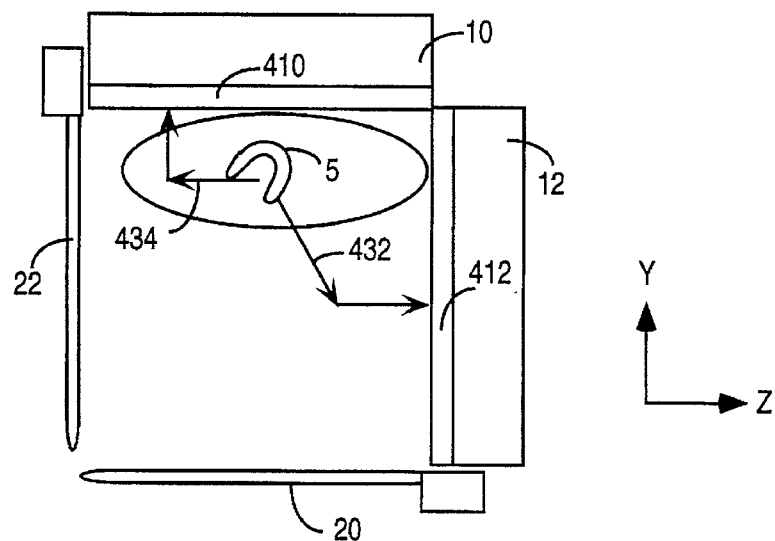
FIG_12A
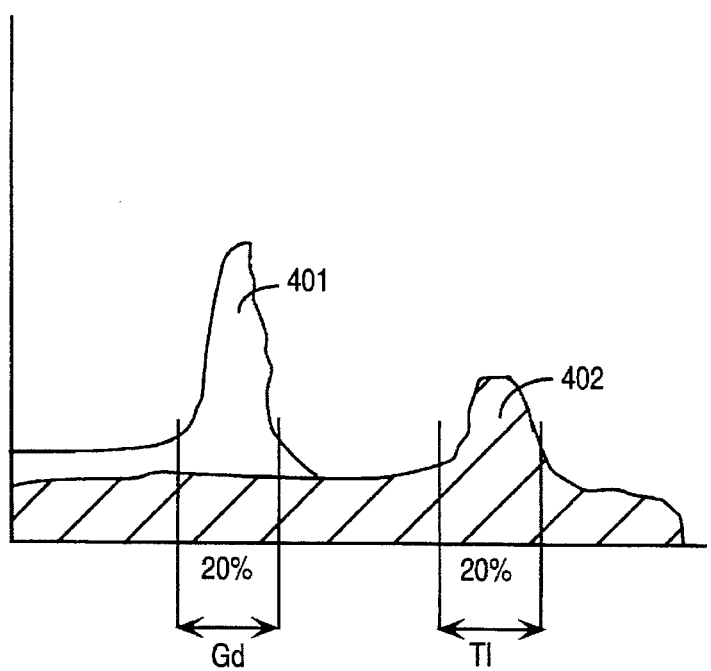
FIG_12B

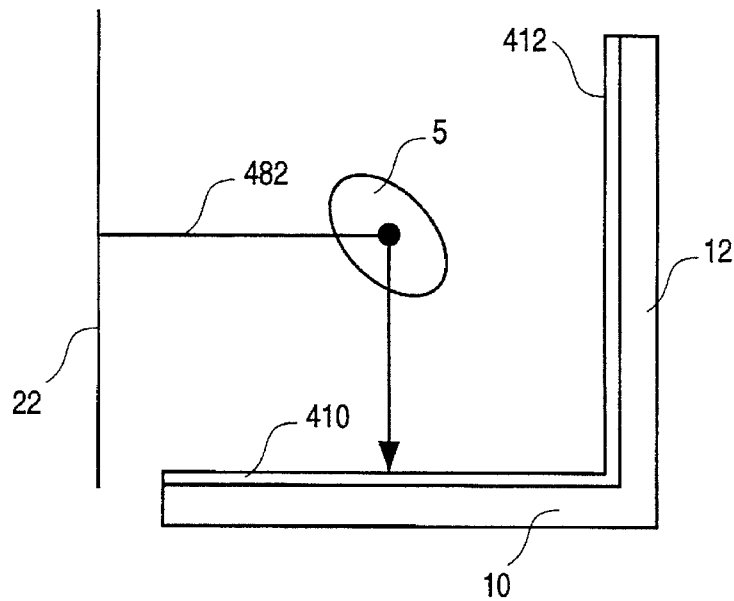
FIG_13A
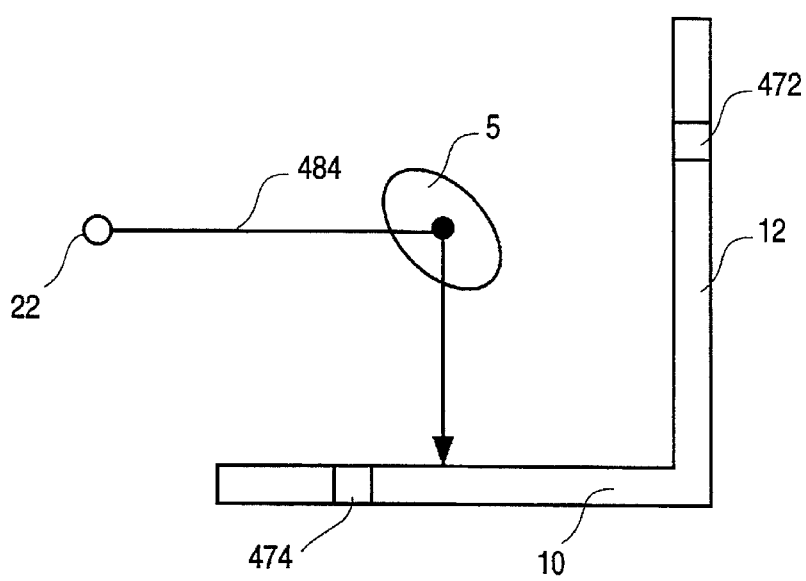
FIG_13B

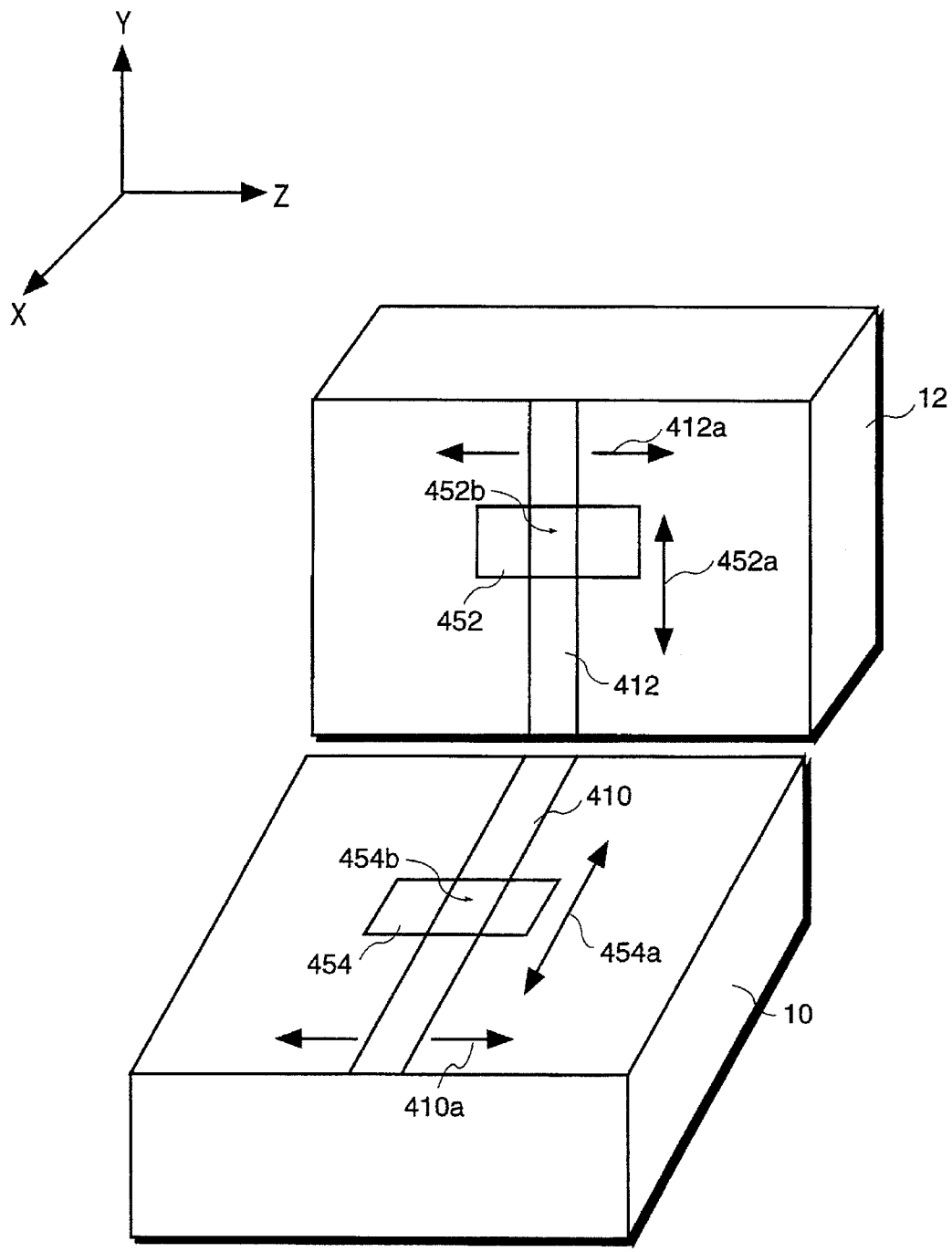
FIG_14A

SCAN SPEED FOR TRANSMISSION EXPOSURE REDUCTION IN A NUCLEAR MEDICINE CAMERA

BACKGROUND OF THE INVENTION

1. Field of the Invention

The present invention relates to the field of nuclear medicine. Particularly, the present invention relates to the field of transmission scanning to provide nonuniform attenuation correction within a gamma camera system.

2. Background of the Invention

Non-uniform photon attenuation is an important factor that affects the quantitative accuracy of images collected using Single Photon Emission Computerized Tomography (SPECT) camera systems and can decrease the sensitivity of these systems for lesion detection. Nonuniform photon attenuation distorts images by interfering with and partially absorbing the radiation emitted from an organ containing a radio-pharmaceutical. Photon attenuation within SPECT systems tends to degrade images by also introducing image artifacts and other distortions that can result in false positive detection or the undetection of lesions. The effects of photon attenuation are especially complex in cardiac studies as a result of nonuniform attenuation attributed to the thorax.

In transmission scanning, the source of radiation is directed toward the associated scintillation detector through the object of interest or patient. If the radiation field is significantly larger than the patient, the radiation source is allowed to directly radiate the detector, causing a high count rate in the scintillation detector. Those parts of the detector that become directly radiated are called unobstructed portions of the detector. It is not advantageous to allow large unobstructed detector areas because the resultant increase in count rate can lead to image degradation and in some cases the event detection electronics and processes can become overloaded (e.g., due to pulse pile-up) and temporarily terminate operation. These high count rates tend to reduce the imaging performance of the imaging system by loading down the signal detection and processing circuitry of the gamma camera.

Transmission computed tomography (TCT) can be used as a method for generating a nonuniform attenuation correction distribution. The transmission image data is gathered using a known source (e.g., line, sheet, or flood) of radiation. If performed separately from the SPECT emission study, the collection of the transmission data requires additional data acquisition time and the collection of the transmission and emission data is susceptible to misregistration effects due to patient (e.g., "object") movement between the data gathering sessions.

However, whether the transmission data is collected simultaneously with the collection of the emission data or not, the patient is generally exposed to additional radiation in order to collect the transmission data. Depending on the size and shape of the patient, different amounts of transmission radiation are required in order to collect the minimum required amounts of transmission data. Systems overexpose the patient with transmission radiation in order to obtain the minimum required amount without regard to the shape or size of the patient. What is needed is a system that can effectively minimize the exposure period of the patient to radiation utilized in collection of the transmission data by considering the particular size and shape contributions of the patient. The present invention offers such advantageous solutions.

Accordingly, it is an object of the present invention to provide improvements within gamma camera systems utilizing nonuniform attenuation correction techniques for improved image quality generation. It is an object of the present invention to determine the minimum exposure time required for the most attenuating portion of a scanned object during a transmission study. It is an object of the present invention to provide the above while considering the size and shape contributions of a particular patient. It is another object of the present invention to provide a reduced radiation exposure period for generation of transmission data used in creating a nonuniform attenuation correction distribution. These and other objects of the present invention not specifically mentioned above will become clear upon discussions of the present invention herein.

SUMMARY OF THE INVENTION

A scan speed procedure and method is described wherein a minimum radiation exposure period is determined on an object by object basis for a transmission study. Two transmission scan phases are performed including a prescan followed by a second transmission scan phase. The first scan consists of a transmission prescan performed using a radiation source over the object. This prescan is of a rapid and predetermined duration (Tp). A resultant count density associated with the object is then generated and examined. The portion having the smallest count density (Cm) is determined and a value (Co) representing the minimum required number of counts for transmission study is given. From the above, a transmission period (Ts) is determined by the system and the second transmission phase (a multi-pass scan phase) is performed for the duration Ts. The computed duration Ts represents the minimum exposure duration required to collect transmission data to ensure that the count density distribution associated with the object will contain at least Cm count density over each portion of the object.

Specifically, embodiments of the present invention include an mechanism for collecting transmission data associated with an object, the mechanism including: a scintillation detector for receiving radiation and reporting image information; a line source of radiation for emitting transmission radiation through the object to the scintillation detector; a processor coupled to receive information from the scintillation detector and coupled to control the line source of radiation, the processor for controlling the line source of radiation to perform a first transmission prescan phase over the object for a first duration and generating in response thereto a first count density information; the processor for computing a second duration for a second transmission scan phase based on the first count density information; the processor for controlling the line source of radiation to perform the second transmission scan phase over the object for the second duration and generating in response thereto a second count density information, the second duration representing a minimum duration of exposure of the object required for generating the second count density information; the processor for generating a set of attenuation correction factors based on the second count density information, the set of attenuation correction factors for use in correcting image data gathered by the scintillation detector during emission scanning; and a memory unit coupled to store and provide access to the first and the second count density information.

Embodiments of the present invention include the above and wherein the second count density information is a distribution over different portions of the object and wherein the processor is for receiving, as input, a minimum count density wherein the distribution contains at least the minimum count density for each portion of the object, wherein the processor is for analyzing the first count density information and determining a minimum observed count density in response thereto wherein the minimum observed count density corresponds to a portion of the object that exhibits maximum attenuation and wherein the processor determines the second duration according to the procedure:

$$Ts = Co \frac{Tp}{Cm}$$

wherein Ts is the second duration, Co is the minimum observed count density, Tp is the first duration, and Cm is the minimum count density.

Embodiments of the present invention include in a nuclear camera system having a pair of scintillation detectors for receiving radiation and reporting image information; a pair of radiation line sources each for emitting transmission radiation through an object to an associated scintillation detector; and a computer system, a computer implemented method of collecting transmission data associated with the object, the method including the steps of: obtaining a minimum count density value desired for each portion of a resultant count density distribution; controlling the pair of radiation line sources to perform a first transmission prescan phase over the object for a first predetermined duration and generating in response thereto a first count density distribution; computing a second duration for a second transmission scan based on the first count density distribution; controlling the pair of radiation line sources to perform the second transmission scan phase over the object for the second duration and generating in response thereto the resultant count density distribution, the second duration representing a minimum duration of exposure of the object required to generate the second count density distribution; and generating a set of attenuation correction factors based on the second count density information, the set of attenuation correction factors for use in correcting image data acquired during emission scanning.

BRIEF DESCRIPTION OF THE DRAWINGS

FIG. 8C illustrates a side cross-sectional view of a line source assembly of the present invention with variable filter configuration.

FIG. 8D illustrates an outside perspective view of a line source assembly of the present invention with variable filter configuration and illustrates control rods and actuating motors.

FIG. 9 is a flow diagram of an operational use of the variable filter embodiment of the present invention for ECT sessions.

FIG. 10A, FIG. 10B, and FIG. 10C, illustrate transmission scan progression of the present invention transverse orientation dual line source transmission scanning configuration.

FIG. 11A illustrates transmission cross-scatter effects and elimination using the present invention transverse orientation dual line source transmission scanning configuration. FIG. 11B illustrates photopeak energy distributions for emission/transmission energy level photons.

FIG. 12A illustrates emission cross-scatter effects and elimination using an alternative embodiment of the present invention transverse orientation dual line source transmission scanning configuration. FIG. 12B illustrates photopeak energy distributions for emission/transmission energy level photons.

FIG. 13A and FIG. 13B are cross section diagrams illustrating differences between the present invention transverse orientation dual line source transmission scanning configuration and an axial configuration.

FIG. 14A is an illustration of the tracking zoom windows and the scanning transmission detection windows of the present invention.

DETAILED DESCRIPTION OF THE INVENTION

Figure 1:
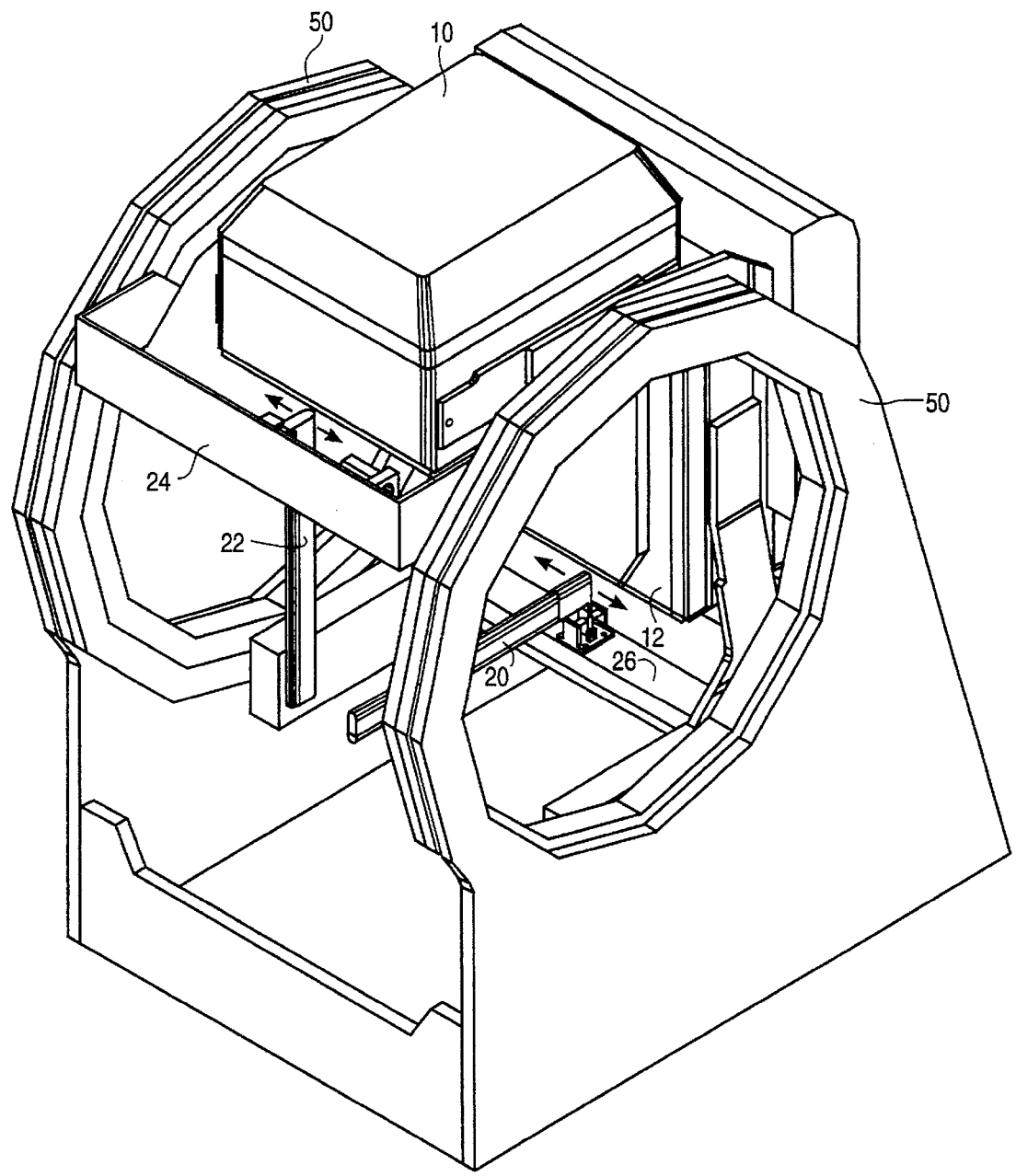
FIG. 1 is an illustration of the dual head detector system of the present invention with the line source assemblies configured for scanning and the detectors at 90 degrees configuration.

In the following detailed description of the present invention, numerous specific details are set forth in order to provide a thorough understanding of the present invention. However, it will be obvious to one skilled in the art that the present invention may be practiced without these specific details. In other instances well known methods, procedures, components, and circuits have not been described in detail as not to unnecessarily obscure aspects of the present invention. Unless specifically stated otherwise as apparent from the following discussions, it is appreciated that throughout the present invention, discussions relating to functions of the computer system of the present invention utilizing terms such as "processing" or "computing" or "calculating" or "determining" or "displaying" or the like, refer to the action of a computer system, or similar electronic computing device, that is executing a program to manipulate and transform data represented as physical (electronic) quantities within the computer system's registers and memories into other data similarly represented as physical quantities within the computer system memories or registers.

I. NONUNIFORM ATTENUATION CORRECTION SYSTEM

Embodiments of the present invention relate to the collection, generation and usage of nonuniform attenuation correction factors used to improve gamma camera imaging. Since each patient that is imaged by a nuclear medicine gamma camera is different (e.g., differently shaped with different sizes, etc.) the tissue and bone structure that surround an organ of interest is different for each patient. This surrounding tissue and bone structure attenuates the radiation emitted from a radiopharmaceutical distributed within the imaged organ. The attenuation of the radiation is nonuniform because the attenuation coefficients of the different tissues and bone are different. Radiation attenuation nonuniformly reduces the count density in the image. This attenuation can lead to falsely identifying an artifact when in fact healthy tissue is imaged and vice-versa. If an artifact is improperbly diagnosed as a lesion, this can lead to invasive measures which are painful and potentially dangerous (e.g., involves a health risk) for the patient.

Nonuniform attenuation caused by the body can be compensated for if the attenuation map of the body is known. Transmission scanning allows a gamma camera and a processing computer system to generate a nonuniform attenuation map of a particular object. This nonuniform attenuation map can be obtained for each rotation angle of a scintillation detector so that a reconstruction algorithm can use the attenuation map for each angle. Generally, during transmission scanning, a source of known radiation is emitted through the patent to be scanned and then the radiation is detected by a scintillation detector. By measuring the intensity of the radiation emitted from the source, and by measuring the intensity of radiation emitted through the object at different ECT angles, the gamma camera's computer system can determine the extent of nonuniform radiation attenuation over different parts of the body. From this, a nonuniform attenuation correction map of the body can be determined using well known methods and procedures. The nonuniform attenuation correction map is used to correct emission image data collected during emission studies.

Embodiments of the present invention are directed at improving the collection and use of transmission data for use in generating nonuniform attenuation correction factors to improve emission image data.

A. DETECTOR SYSTEM

The detector system of an embodiment of the present invention is illustrated in FIG. 1. This is a dual head implementation, however, embodiments of the present invention can operate equally effective within a single or other multi- head embodiment. Regarding the dual head implementation, two scintillation detectors 10 and 12 are installed within the gantry (e.g., between gantry rings 50) and are rotatable about the center of the gantry ring 50. Each scintillation detector contains a crystal layer and an array of photomultiplier tubes, each PMT generates a separate channel signal responsive to light energy released by the crystal layer in response to a gamma interaction therein. As shown in FIG. 1, the detectors are at a 90 degree angle with respect to each other. A table (not shown) is placed into the gantry ring 50 and a patient rests on top of the table for imaging. Channel signals from the detectors are then sent to signal processing hardware 120 and to a computer system 112 for image processing (including corrections), see FIG. 4.

The detectors 10 and 12 of FIG. 1 can contain event detection circuitry that transforms the signals from the photomultipliers to digital signals representative of the spatial coordinate of each detected event and the event energy. This logic can also be externally located (for instance, see FIG. 4, signal processing hardware 120). An event, or "count" is reported by the detectors to a computer system 112 for correction, analysis, storage and image generation. The detectors can collect and report radiation that is emitted from a patient (e.g., emission image data) and can also collect and report radiation emitted form a line source (transmission image data). Transmission data is utilized, among other things, for generation of attenuation correction distributions to compensate for nonuniform attenuation attributable to the patient (e.g., the chest region in cardiac studies).

A separate radiation emitting line source (with collimator) is mounted and associated with each scintillation detector. For instance, line source assembly 22 is associated with detector 12 and line source assembly 20 is associated with detector 10. Also, line source assembly 22 is mounted on rail 24 and the base of line source assembly 22 can move along the long axis of rail 24, as shown in order to displace ("scan") across the field of view of the associated detector. Likewise, line source assembly 20 is mounted on rail 26 and the base of line source assembly 20 can move along the long axis of rail 26, as shown in order to displace ("scan") across the field of view of the associated detector. It is appreciated that when the detectors rotate about the center of gantry ring 50, the associated emission line source will rotate in like form and degree. The line sources are utilized by the present invention for irradiating a patient in order to gather transmission data for the generation of the nonuniform attenuation correction map that is stored in memory for the patient. The nonuniform attenuation correction map is used to compensate for nonuniform attenuation of the emission data which is also collected by the present invention detectors 10 and 12.

Figure 2:
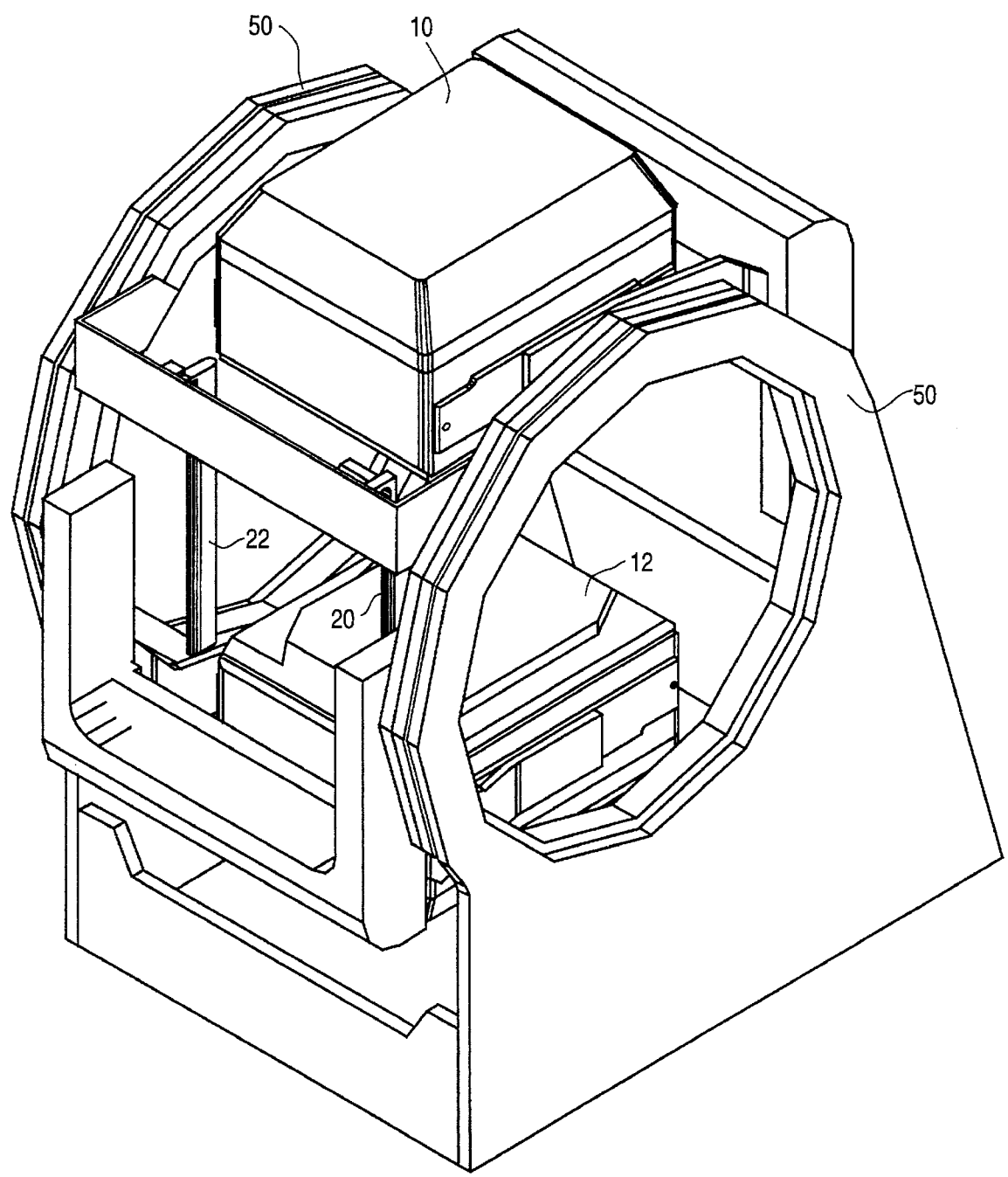
FIG. 2 illustrates the dual head detector system of the present invention with the line source assemblies withdrawn for storage and the detectors at 180 degrees configuration.

The scintillation detectors 10 and 12 can rotate about the gantry 50 so such that they are in the positions (180 degree orientation) shown in FIG. 2. FIG. 2 also illustrates the line source assemblies 22 and 20 in their storage position.

Figure 3:
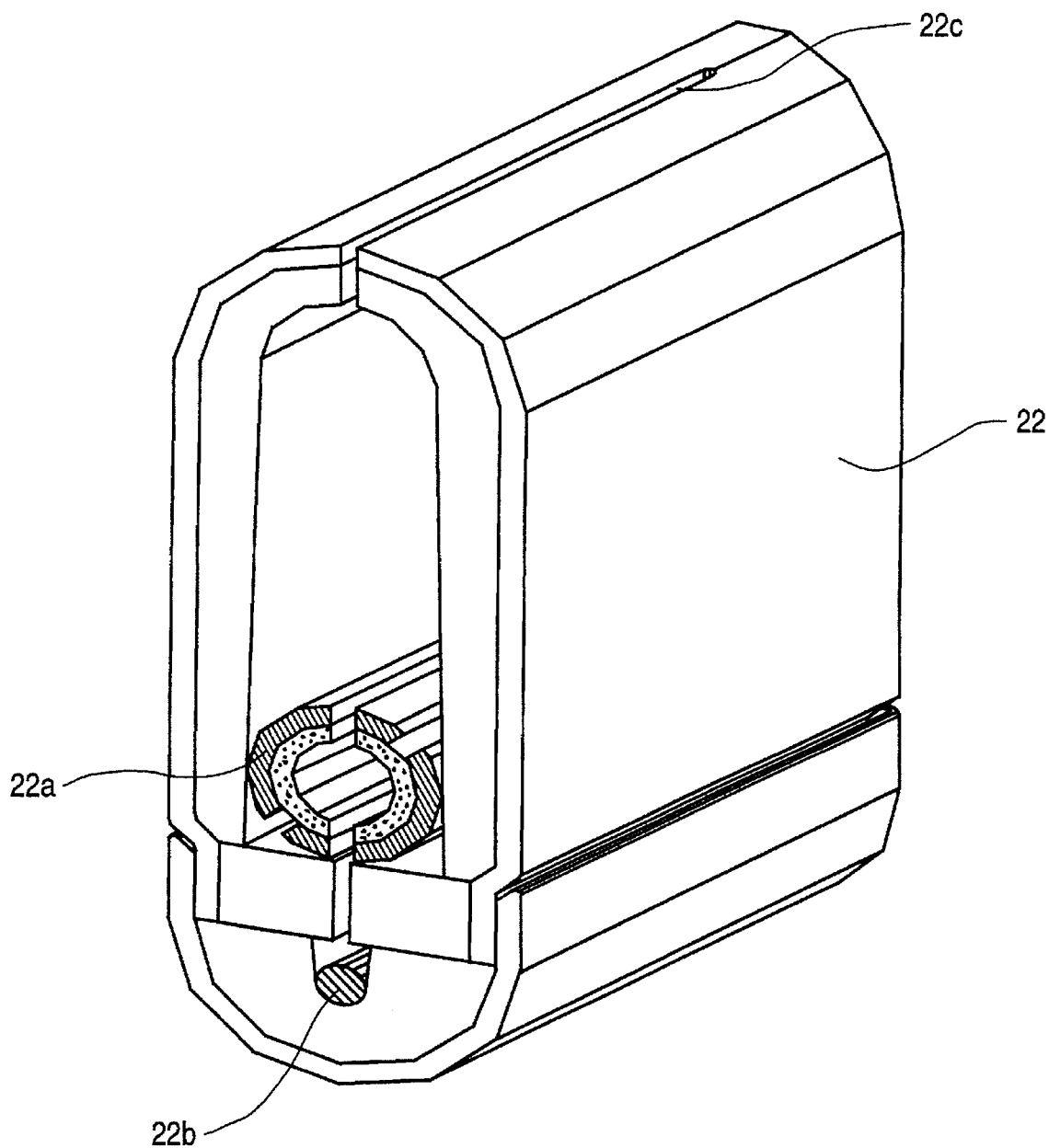
FIG. 3 is an illustration of a cross sectional view of a line source assembly of one embodiment of the present invention.

FIG. 3 illustrates a cross section of an exemplary design of the scanning line source assembly 22 of one embodiment of the present invention in more detail (line source assembly 20 is similar). The radiation emitting source or rod is shown as 22b. The radiation is emitted through a small aperture and then through a shutter 22a that rotates to vary the amount of radiation emitted. Radiation is allowed pass through small openings places on either side of the shutter 22a. The radiation then exists via slot (collimator) 22c. Different types of line sources 22b can be utilized within the scope of the present invention, including a Tc-99m filled line source or a line source using Gd-153, Am241, or Co-57. Generally, the transmission source should be of a different photo peak energy than the emission source. As will be discussed in further herein, various embodiments of the present invention include special radiation filters within the line source assemblies.

B. COMPUTER PROCESSOR SYSTEM

Figure 4:
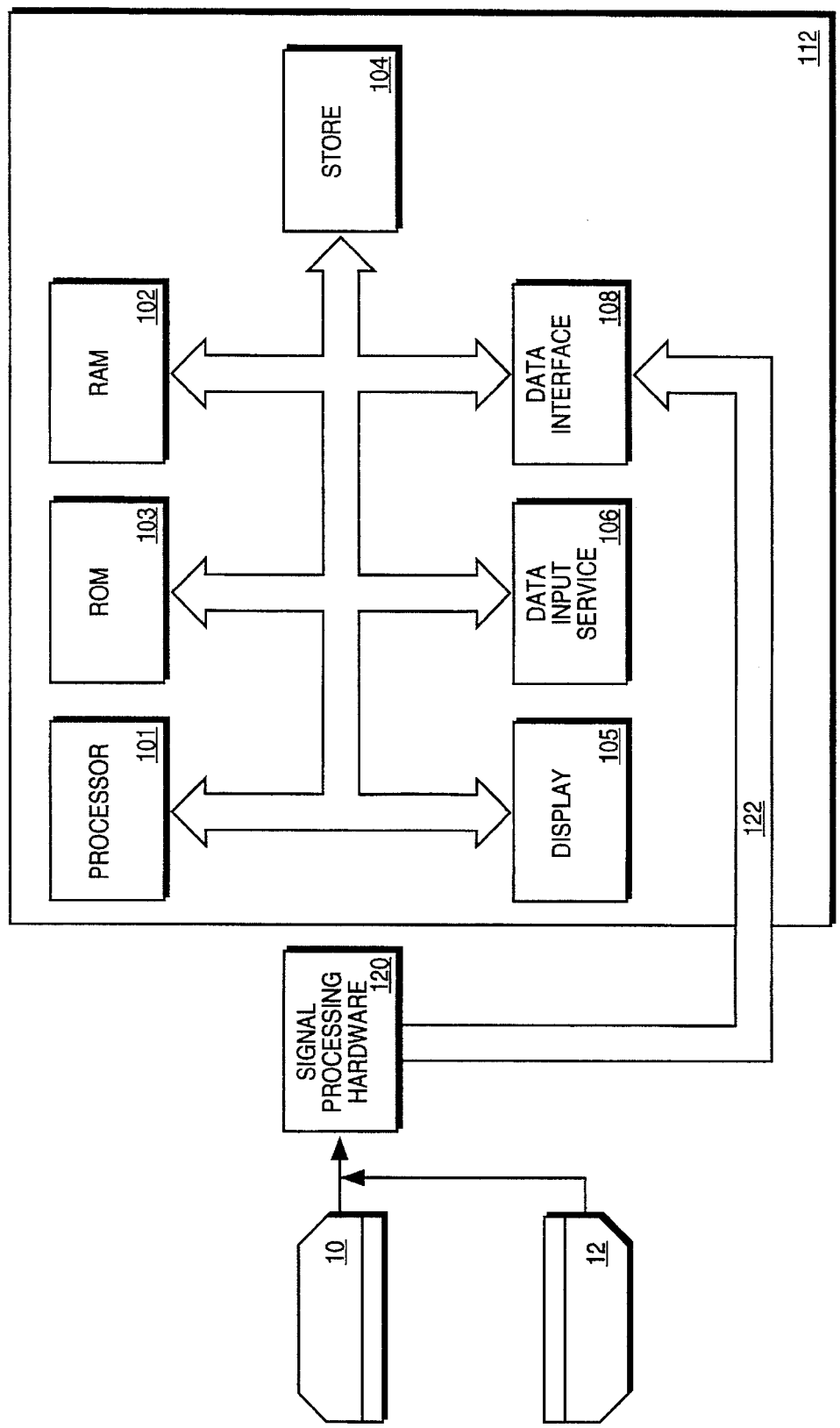
FIG. 4 illustrates a block diagram of a general purpose computer system coupled to the detector system electronics of the present invention.

Refer to FIG. 4 which illustrates components of a general purpose computer system 112 used by the present invention for processing image information supplied from gamma camera detectors 10 and 12. The general purpose computer system 112 is capable of performing image processing functions (e.g., processing emission and transmission data). The computer system 112 comprises an address/data bus 100 for communicating information within the system, a central processor 101 coupled with the bus 100 for executing instructions and processing information, a random access memory 102 coupled with the bus 100 for storing information and instructions for the central processor 101, a read only memory 103 coupled with the bus 100 for storing static information and instructions for the processor 101, a data storage device 104 such as, a magnetic or optical disk and disk drive coupled with the bus 100 for storing image information and instructions, a display device 105 coupled to the bus 100 for displaying information to the computer user, an alphanumeric input device 106 including alphanumeric and function keys coupled to the bus 100 for communicating information and command selections to the central processor 101, a cursor control device (part of the data input device 106) coupled to the bus for communicating user input information and command selections to the central processor 101, and a communication device 108 coupled to the bus 100 for communicating command selections to the processor 101. A hardcopy device (e.g., printer) may also be coupled to bus 100.

The display device 105 of FIG. 4 utilized with the computer system 112 of the present invention may be a liquid crystal device, cathode ray tube, or other display device suitable for creating graphic images and alphanumeric characters recognizable to the user. The cursor control device allows the computer user to dynamically signal the two dimensional movement of a visible symbol (pointer) on a display screen of the display device 105. Many implementations of the cursor control device are known in the art including a trackball, finger pad, mouse, joystick or special keys on the alphanumeric input device 105 capable of signaling movement of a given direction or manner of displacement.

The computer system 112 of FIG. 4 interfaces with the gamma detector 10 and 12 via signal processing hardware circuits 120 over bus 122. The signal processing hardware 120 can compose amplification circuitry and analog to digital conversion circuits for converting channel signals from the detectors to digital data for transmission to the computer system 112. It is appreciated that channel signal information from the detectors 10 and 12 are converted into count density information by the computer system 112 and stored within the computer's memory 102 in matrix form, depending on the type of imaging session performed. This is true for both transmission and emission data. Nonuniform attenuation correction maps are stored in the computer memory 102 as well. The signal processing hardware 120 converts photomultiplier output into spatial coordinate data and event energy for detected events. Events within similar spatial coordinates are "binned" together in the memory 102 of the computer system in order to generate image information and form count density information.

This image information is collected in the form of a matrix of N rows by N columns. The size of the detector's effective field of view and the number of rows and columns of a particular matrix define the "size" of a pixel of the matrix. A pixel corresponds to one cell or "bin" of the matrix. Image matrices are generally collected at different ECT angles and then a reconstruction is done, using tomographic reconstruction to generate a three-dimensional image of an organ.

It is appreciated that the computer system 112 also controls movement of the detectors on the gantry ring 50 and also controls line source motion controllers for controlling the movement of the line sources 20 and 22.

Although the scintillation detectors 10, 12 are capable of reporting scintillation events with great accuracy, the computer system 112 collects and interprets the data depending on reference matrix sizes (e.g., 64×64, 128×128, 512×512 and 1024×1024). These sizes are programmable. Further, a given matrix size can be allocated to certain portions of the field of view of the detector. For instance, in a cardiac study, a 512×512 matrix can be allocated to only the region of the detectors' field of view that covers the heart. Therefore, when data is received from the scintillation detector regarding the energy and location of a detected interaction, this information is "binned" (e.g., placed) into the appropriate matrix entry that corresponds to the location of the interaction as reported by the detector. Count information reported by the detectors is binned into memory 102 and image data is taken from there. This is true for both transmission and emission data.

II. SCAN SPEED EMBODIMENT

The present invention includes a scan speed embodiment wherein a minimum exposure time period is determined, patient by patient, for exposure to radiation emitted from the scanning line sources 20 and 22 for collection of transmission data. Patients vary by thickness and the more thick the patient, the more the patient needs to be irradiated to gather sufficient transmission data due to transmission radiation attenuation. However, the present invention determines the minimum dosage of radiation required to obtain sufficient transmission image data in order to reduce exposure time on a patient by patient basis. To promote the health of the patient, it is advantageous to reduce this exposure time to the patient. In order for the nonuniform attenuation correction map to be properly determined by the present invention (and there are a number of different ways in which this data can be computed) each elemental bin ("cell" or "pixel") of the image matrix for the patient must collect a certain minimum number of counts as a result of the transmission exposure. Using the reported transmission data, from a pre-scan phase, and knowing the original exposure of radiation, the gamma camera system of the present invention can determine a nonuniform attenuation correction map of the patient. Mechanisms for computing attenuation correction maps based on the above information are well known.

If there are more than the minimum number of counts per bin as a result of the transmission exposure, then the nonuniform attenuation correction distribution can still be properly computed, but the patient will be exposed to an unnecessary dosage of radiation to collect the transmission data. This embodiment of the present invention determines the particular dosage of radiation (e.g., exposure time) required in order to not unnecessarily expose the patient to transmission radiation.

Generally, in order to perform the above, the present invention provides two different transmission scan sequences or "phases." A first or "prescan" phase is performed and is a rapid single pass scan of low radiation dosage performed to obtain the minimum count density measured as a result of the prescan. Although a single pass scan is utilized for the prescan phase under the preferred embodiment of the present invention, multiple scan passes can also be contemplated within the scope of the present invention. The information of the prescan phase determines the duration of the normal transmission scan, which is the second transmission scan phase. The normal transmission scan is used to generate a nonuniform attenuation correction map. This process is explained in further detail below. It is appreciated that under the preferred embodiment of the present invention, the second or "normal" transmission scan phase is a multi-pass scan phase.

Figure 5:
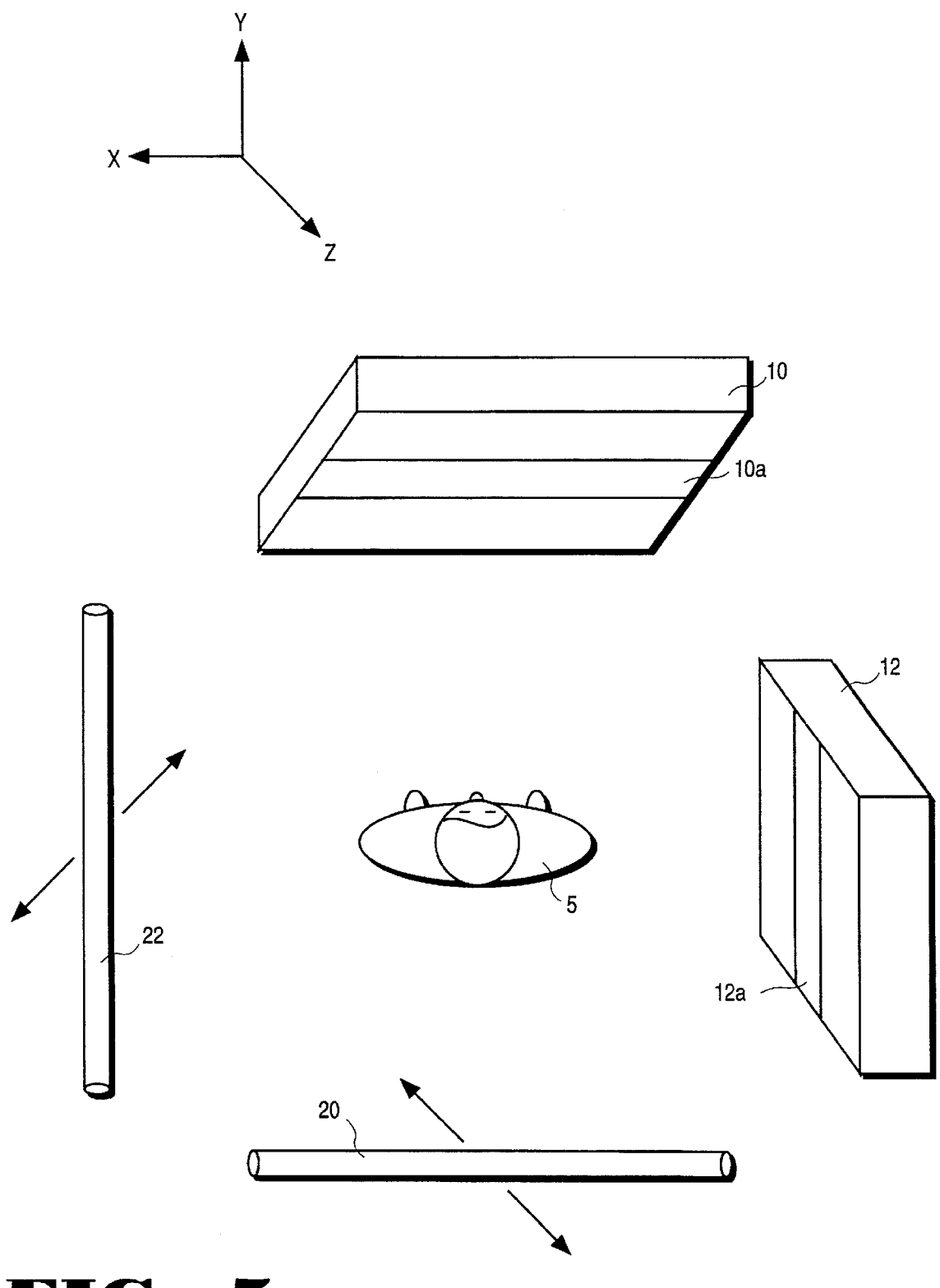
FIG. 5 is an illustration of an exemplary configuration for performing a speed scan operation within the present invention.
Figure 6:
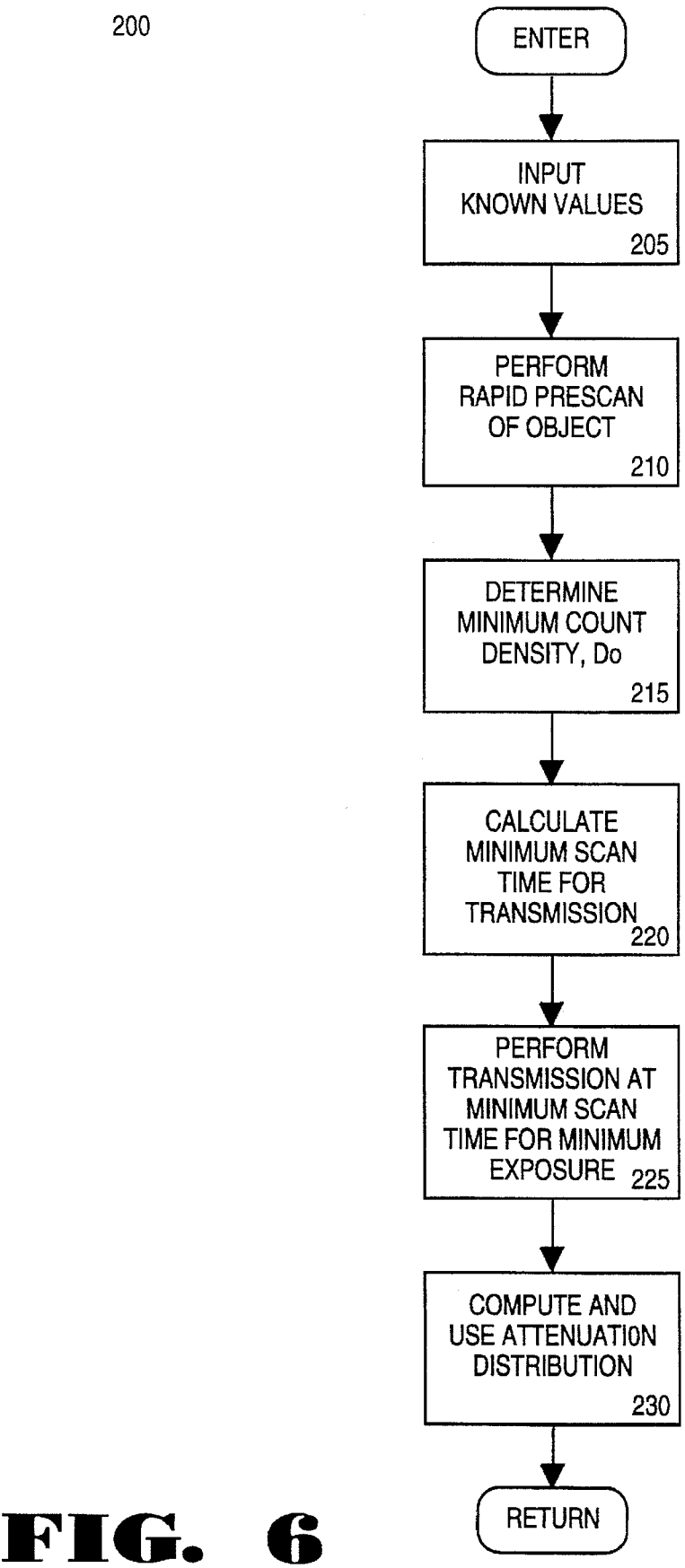
FIG. 6 is a flow diagram illustrating process steps for performing a speed scan operation within the present invention.

The processing 200 of this embodiment of the present invention is performed via general purpose computer system 112 and is illustrated with respect to FIG. 6. Within the discussions of process 200, reference is also made to FIG. 5 and FIG. 7. The process 200 enters and at the first block 205, the known values are input from the data input device 106. The known values input at block 205 consist of (1) the minimum required counts per bin, Co, (which is also called the minimum count density) and (2) the time period for the prescan transmission radiation, Tp. The minimum required counts per bin, Co, in order to compute the nonuniform attenuation correction distribution will vary depending on the type of nonuniform attenuation correction map desired and the type of scan performed. Since this embodiment of the present invention can effectively operate to generate a number of different types of attenuation distributions based on a number of different types of scans, there is no specific minimum count number. However, with respect to the disclosed embodiment herein, the exemplary minimum number of counts is 20 to 30 (e.g., Co=20–30).

Also, in one embodiment, the prescan exposure duration is programmable depending on the type of prescan performed and the type of nonuniform attenuation correction map desired. With respect to the disclosed exemplary embodiment, this value is in the range of 5–15 seconds (Tp=5–15). It is appreciated that at block 205, the values Co and Tp can be programmed into computer system 112 as default values and therefore no data input is required unless these defaults are to be altered.

At block 205, the patient is placed onto a table and placed with the gantry ring 50. The scintillation detectors are arranged such that they will image different views of the patient. This can be performed a number of different ways and an exemplary arrangement is illustrated in FIG. 5. As shown in FIG. 5, the view is looking into the gantry ring structure 50 of the detector system (at the head of the patient 5 located along the Z axis). Scintillation detectors 10 and 12 are oriented at right angles to each other with detector 10 on top and detector 12 at the side. Line source assembly 20 scans the patient down the Z axis while the surface of detector 10 is above and within the XZ plane.

Transmission detection region 10a receives collimated radiation as the scanning line source assembly 20 travels down axis Z. Region 10a scans in synchronization with assembly 20. Similarly, line source assembly 22 scans the patient down the Z axis while the detector 12 is within the YZ plane. Transmission region 12a receives collimated radiation as the scanning line source assembly 22 travels down axis Z. Region 12a moves in synchronization with assembly 22. During the prescan operation, the time period required for the scanning line sources to move completely down the Z axis to radiate the patient 5 is the prescan time Tp. Therefore, the shorter the period selected, the faster the line sources move during the prescan and the longer the period, the slower the line sources move during the prescan. After the prescan, the two line sources 20 and 22 will again scan the patient 5 during the normal transmission scan.

Referring back to FIG. 6, with the patient 5 placed in the gantry and the time period Tp selected, the present invention at block 210 prescans the patient, under computer system 112 control, by having both line sources 22 and 20 radiate the patient 5 while moving along the Z axis. Detectors 12 and 10 collect and report the transmission data via regions 10a and 12a to the computer system 112. When the prescan of block 210 is complete, the computer system stores a first count density information and then computer system 112 analyzes this transmission data at block 215 to determine the minimum count density measured, Cm, as a result of the transmission exposure.

Figure 7:
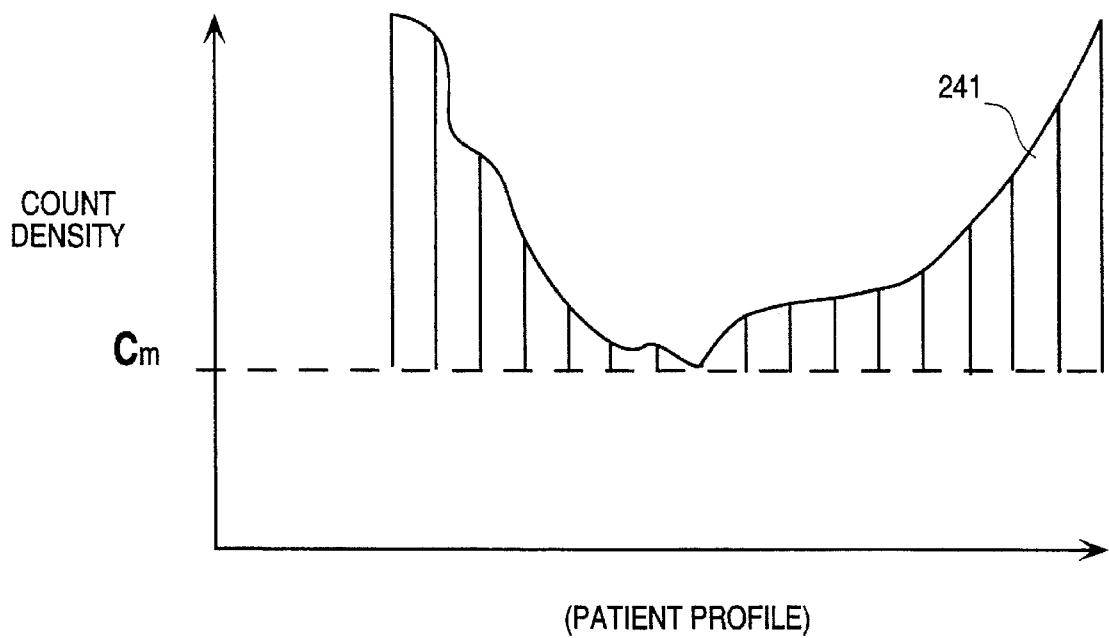
FIG. 7 illustrates a count density relationship for a given patient profile within the scan speed operation of the present invention.

FIG. 7 illustrates an exemplary transmission map and shows count density versus the patient profile. Computer system 112 stores the "prescan" transmission map in memory 102. The map can also be stored in disk 104. Typically the side portion of the patient is the most attenuated portion and therefore contains the smallest count density measured, Cm. As the patient is thinner at the edges, the count density is larger at these parts of the profile. As the patient is thicker at the center, the count density is smaller at these regions. The result of the patient profile 241 is a U shaped "prescan" transmission map as shown in FIG. 7. It is appreciated that a number of different methods and mechanisms are known in the art to compute a transmission map and different maps can be generated. For instance, a transmission map can be computed in three dimensional space (by gathering transmission data with ECT motion), the transmission map can be presented based on patient profile. Regardless of the way in which the "prescan" transmission data is presented, the present invention at block 215 determines the portion of the patient that most attenuates the transmission exposure. The count density of the "prescan" transmission map at this portion is the minimum count density measured by the prescan, Cm. At block 215, therefore, the "prescan" transmission map 241 is measured and the lowest measured count density, Cm, is recorded to memory 102.

At block 220, the present invention computes the minimum scan time required to perform the normal transmission scan that is used to generate the nonuniform attenuation correction factors of the present invention. The following relationship is utilized:

$$\frac{Tp}{Cm} = \frac{Ts}{Co}$$

Wherein the ratio between the time period of exposure for the prescan transmission exposure period (Tp) over the measured minimum count density for this prescan transmission (Cm) should be equal to the ration between the minimum time required to perform the normal transmission exposure (Ts) over the minimum count density required to perform the normal transmission exposure (Co). The values Co and Tp are input at block 205. The value Cm is computed at block 215. The above relationship can be rewritten as:

$$Ts = Co \frac{Tp}{Cm}$$

The computer system 112 at block 220 performs the above procedure in order to compute Ts, the minimum exposure time period required to insure that the minimum required count density, Co, is acquired by the normal transmission exposure scan time, Ts. At this time period, Ts, the part of the patient causing the most attenuation in the transmission data will still allow the collection of the minimum counts required of transmission data for generating a sufficient nonuniform attenuation correction map.

At block 225, the present invention computer system 112 directs the detector system to perform a normal transmission scan phase of the patient (similar to the scan performed in block 210), however, the normal transmission scan is performed using an exposure period of Ts. As discussed above, the second or "normal" transmission scan phase is a multi-pass scan phase across various angles of rotation around the patient. As a result of this normal transmission exposure, transmission data is collected by both detectors 10 and 12 at different projection angles and a normal transmission map (a second count density) is generated at block 230. From this, a nonuniform attenuation correction distribution is utilized for the correction of emission image data collected from the patient. The nonuniform attenuation correction map is stored in memory 102.

Utilizing the above procedure, the patient 5, is exposed to the minimum required radiation dosage during the normal transmission exposure. This is advantageous because of the varying thickness of different patients. If one exposure dosage was developed for all patients, smaller patients would be subjected to an unnecessarily long transmission exposure or larger patients would not have enough exposure to provide a usable attenuation correction map. Therefore, since the present invention determines the optimum exposure dosage on a patient by patient basis, each patient receives the minimum transmission dosage required to generate a sufficient nonuniform attenuation correction distribution.

The above procedure can be utilized with respect to a single transmission scan across a patient at a known or given angle relationship with respect to the detector and the patient. However, this technique is extended to include determining the minimum transmission exposure durations required (for each angle) within a transmission session involving ECT motion. This aspect of the present invention involves performing the prescan (of duration Tp) with both line source 20 and line source 22 in order to determine a minimum measured count value for both the anterior and lateral dimensions for a given object during the prescan. In other words, a Cm(anterior) and a Cm(lateral) can be obtained, one from each scintillation detector, during the prescan. By dividing the above count densities by the prescan Tp duration, a count rate can be determined for both the anterior and lateral dimensions. These count rates are expressed as Cr(anterior) and Cr(lateral).

$$Cr(anterior) = Cm(anterior)/Tp$$

$$Cr(lateral) = Cm(lateral)/Tp$$

Based on a body contour of the object (e.g., cross sectional profile of object) in conjunction with the lateral and anterior measured count rates, a particular transmission count rate can be determined by the computer system 112, using geometry, for each angle of rotation for an ECT scan. This count rate for a given angle is the transmission rate through the body for that given angle. This count rate value can be expressed as Cr(i), where (i) is the angle of rotation for a given ECT scan angle. The count rate for each angle, Cr(i), depends on the width and length of the object which can be supplied via the contour information. A number of well known techniques can be utilized to obtain body contour data.

Given the count rate, Cr(i), for each ECT angle, i, and given the minimum number of counts required for a given transmission scan, Co, the computer system 112 can compute the minimum time required for transmission at each ECT angle, Ts(i), according to the below relationship:

$$Ts(i) = Co/Cr(i)$$

The transmission duration, Ts(i), for each angle is then stored in the memory 102 of the computer system 112, for a given angle of rotation, i, the present invention will only expose the patient to the transmission radiation for a duration of Ts(i). This process continues until each angle of rotation is complete. Based on this information, a reconstruction is performed by the computer system 112 (using well known methods and procedures) in order to generate a three dimensional transmission map of the object. From this, a complete nonuniform attenuation correction map is derived for each angle of rotation. This embodiment of the present invention is particularly advantageous in reducing the transmission exposure of the patient because of the number of different transmission exposures (e.g., one for each angle or rotation).

It is appreciated that within the scope of the present invention, as an alternative operation to the above, a uniform scan rate can also be applied across all angles of ECT rotation.

One embodiment of the present invention using the above ECT technique, utilizes two detectors 10, 12 oriented at 90 degrees and uses both line sources 20, 22 to scan along the patient so that anterior and lateral transmission information are simultaneously gathered by each detector, respectively. In such case, the line sources radiate the patient simultaneously during prescan along the patient's long axis. Then the values Cm(lateral) and Cm(anterior) can be computed from the transmission maps of the detectors. As discussed above, using this information the minimum transmission duration can be obtained for each angle of rotation of the detector pair. The normal transmission scan for each angle can then be performed.

III. VARIABLE LINE FILTER EMBODIMENT

The present invention includes a variable line filter embodiment that is utilized within the line source assemblies 20 and 22. For discussion, details of line source assembly 22 are illustrated herein, however, it is appreciated that this discussion applies equally to the line source 20. This embodiment of the present invention involves the use of several differently shaped filters that are rotatably mounted to surround the line source within a line source assembly. A control unit provides for the selection of a particular line source filter that can be rotated into place for different projection angles of a scintillation camera during transmission scanning.

Figure 8A:
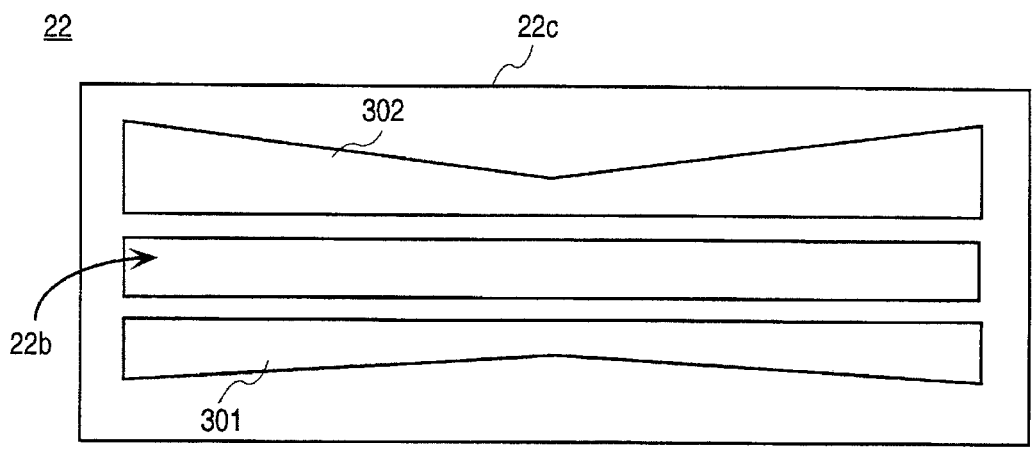
FIG. 8A illustrates a frontal cross-sectional view of a variable filter configuration of the present invention.

Reference is made to FIG. 8A where a simplified diagram (cross section) is made of the line source assembly 22. The line source 22b is shown in the center of the assembly and this source 22b is surrounded by different filters 302 and 301. The collimator slit 22c is shown for orientation. Filters 302 and 301 are mounted such that they can rotate around the line source 22b to an installed position. FIG. 8A shows filter 302 in the installed position. A control unit controls the rotation of the filters around the line source such that different filters can be installed. As shown, filter 302 is larger in dimension than filter 301 and would therefore provide more filter capacity when installed. Although the filters 301 and 302 are shown as wedged shaped (e.g., thicker on the ends and thinner in the mid section), the filter can adopt any general shape or profile within the scope of the present invention.

The purpose of the installed filter is to reduce the high detected count rates which occurs when portions of the transmission line source 22b extend beyond the object 5 being imaged and directly irradiate the scintillation detector 12. As shown in FIG. 8A, the filter is a wedge which is thickest towards the outside of the detector's field of view and reduces thickness toward the inside (center portion) where it is necessary to have maximum flux to penetrate the object 5 being imaged. For different emission projections, where different portions of the line source are directly exposed to the detector, a filter of different shape is rotated into the installed position, as needed. This reduces the count rate toward the outside of the object 5 while allowing the required penetration through the inside of the object. Therefore, the present invention recognizes that a constant filter is not advantageous during an ECT scan where different portions (unobstructed portions) of the detector are directly exposed to the line source as different projection angles are traversed during the scan.

Figure 8B:
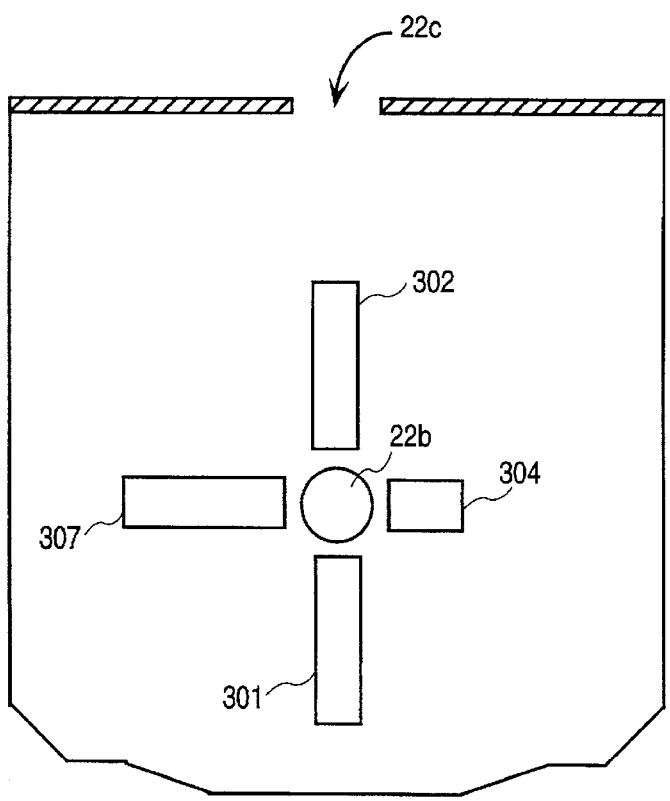
FIG. 8B is an illustration of a cross-section side view of a variable filter configuration of the present invention.

FIG. 8B illustrates another cross sectional view of the simplified line source assembly 22 of the present invention. As shown, the line source 22b is surrounded by four filters 301, 302, 304, 307 of varying size and shape. The filters are rotatably attached together so that they can rotate (clockwise or counter-clockwise) around the line source 22b. During use, at any one time, only one filter is installed. A collimating slit 22c is also shown in the line source assembly 22. The filter 302 is shown in the installed position.

FIG. 8C illustrates a more detailed cross sectional view of a scanning line source assembly 22 of this embodiment of the present invention. As shown, the assembly 22 is composed of an upper cover 22d and a lower cover 22f. There is a lead shielding 22e that is surrounded by the upper cover 22d. The shutter assembly is composed of a lead shielding 22ab that surrounds a steel tubing 22ac. The tubing 22ac is rotatably attached such that it may turn with respect to the lead shielding 22ab. The same is true for the shielding 22ab, it may turn with respect to the tubing 22ac. The collimating slit 22c of the line source assembly 22 is also shown.

FIG. 8C further illustrates a cross sectional view of the line source 22b that is surrounded by a control junction 310. Different types of line sources 22b can be utilized within the scope of this embodiment of the present invention, including a Tc-99m filled line source or a line source using Gd-153, Am241, or Co-57. The multiple filters 301, 304, 302 and 307 are attached to the control junction 310 and in this way are rotatably attached to surround the line source 22b. It is appreciated that there are a number of well known methods for rotatably attaching the filters to surround the line source 22b and the implementation illustrated in FIG. 8C is exemplary. The lower cover 22f surrounds a leading shielding 22g. The filters can be composed of a number of different materials for providing attenuation of the radiation emitted from the line source 22b, and one such material is copper. It is further appreciated that the number of filters that can be attached to the control junction 310 is variable and constrained only due to the size and physical characteristics of the filters and that the illustration of two and four filters herein is exemplary only.

Filter 301 is shown in the installed position and the control junction rotates to install the other filters as needed. The installed filter 301 acts to attenuate the radiation from the line source 22b before the radiation passes through the shutter assembly 22ab and 22ac. Then, the radiation is collimated by slit 22C before exiting the line source assembly 22. It is appreciated that in an alternate embodiment of the present invention, the filter configuration can be placed after the shutter assembly 22ab and 22ac between the shutter assembly and the collimating slit 22c. In such alternate embodiment, the installed filter would be exposed to the radiation while the remainder of the filters are positioned such that they do not interfere with the transmission.

FIG. 8D is an outside view of the line source assembly 22 viewing from the lower cover 22f (which appears on top). The upper cover 22d is also shown. Coupled to the side of the assembly 22 are two control rods 314 and 312. Control rod 312 is coupled to the shutter assembly 22ab and 22ac and controls the opening and closing (or partial opening) of the shutter assembly. Control rod 314 is coupled to the control junction 310 of the filter assembly and controls the rotation of the control junction 310. Control rod 314 therefore controls the rotation of the filters about the line source 22b and will control the installation of a particular filter. Both of the control rods 312 and 314 are actuated by a separate computer controlled motor 312a and 314a, respectively. While many different embodiments of actuators can be used consistent within the scope of the present invention, an exemplary motor of 312a and 314a is capable of rotating both clockwise and counter-clockwise and can be of a stepper motor design that is digitally controlled from a computer system such as computer system 112. Under the above implementation, both the shutter assembly 22ab and 22ac and the filter assembly are computer controlled.

Operational Use of Variable Filter

The following describes the operational use of this embodiment of the present invention variable filter configuration. This embodiment can be used in ECT studies or within studies that do not require ECT motion (such as total body scans). For transmission studies that do not involve ECT movement, the object being scanned can be evaluated to determine the amount of the detector that is unobstructed by the object, and based on this amount, an appropriately sized and shaped filter can be selected to compensate for this unobstructed portion of the detector. Then, either manually or under computer control the proper filter is installed within the line source assembly 22 or assemblies 20 and 22. The amount of the detector that is unobstructed by the object can be determined by using body contour information (see below).

FIG. 9 illustrates a process flow 350 representing an operational use for the variable filter embodiment of the present invention for ECT scans. The process starts at block 354 where the shape of the object is determined to arrive at body contour information. A method and apparatus are disclosed in U.S. patent application Ser. No. 07/981,833, entitled "PROXIMITY DETECTOR FOR BODY CONTOURING SYSTEM OF A MEDICAL CAMERA", and issued on Dec. 27, 1994 as U.S. Pat. No. 5,376,796, for obtaining the profile of an object being scanned. This patent is hereby incorporated by reference. This patent discloses that body contour information is constructed for an object to be scanned by integrating the body profile data. However, it is appreciated that the methodology and apparatus described above for obtaining a body contour is exemplary only and that there are a number of different well known ways to collect such data. In any case, the body contour information is typically stored in a computer system's memory (e.g., RAM 102) so that it can be recalled for future use.

At block 356 of FIG. 9, during an ECT scanning session, for a particular angle of rotation of the scintillation detector the computer system 112 determines the amount of the detector (e.g., 12) unobstructed by the object during a transmission scan wherein the line source assembly (e.g., assembly 22) is radiating. This determination is performed using well known geometric procedures given the known body contour of the object and the angle of rotation of the scintillation detector. The result can be expressed as:

$$Xunobstructed = F(theta, contour)$$

where Xunobstructed is the amount of the detector's field of view that is unobstructed by the object during transmission, theta is the current rotation angle and contour is the body contour database information for the portion of the body being scanned. The above procedure assumes the configuration of the gantry structure (e.g., the position of the detector with respect to the object) and the location of the object being scanned are known. The process required to compute the unobstructed portion of a detector, given the angle of rotation and the contour data, is well known and a number of different geometric relationships can be used consistent within the scope of the present invention.

At block 358 of FIG. 9, the present invention then directs the computer system 112 to select the most appropriate filter to install in order to compensate for the unobstructed portion of the detector and minimize the count density over the unobstructed portions of the detector's field of view. For example, if the ECT rotation angle is low and the side of the object is being scanned, then the unobstructed portion of the detector is large and a filter having relatively thick sides will be used. Or, if the ECT rotation angle is high and the forward portion of the object is being scanned, then a filter is selected having relatively thin and smaller sides. A database can be constructed in memory 104 having a column for the obstructed portion and a column for a corresponding filter type. The computer system 112 then compares the computed unobstructed portions of the detector's field of view (Xunobstructed) to the proper database column until a close match occurs. Then, the computer system selects the proper filter for use based on the corresponding entry of the database. The filter selected is that filter that minimizes the count rate to the unobstructed portion of the detector but allows sufficient count rate through the object for the obstructed detector portion.

At block 360 of FIG. 9, the computer system 112 directs motor 314a to turn control rod 314 to actuate the control junction 310 so that the proper (e.g., selected) filter is installed. It is appreciated that the computer system 112 stores a filter order database indicating the order that the filters are installed on the control junction 310 for selection of the proper filter. Further, an identification circuit can also be employed to automatically report the type of filters and their location within the control junction. Such identification circuits using binary coding are well known in the art.

At block 362, the present invention then instructs the line source assembly (e.g., 22) to perform the required transmission using the proper filter. The shutter assembly 22ab 22ac is then allowed to open. At block 364, the present invention is then determines if more ECT rotation angles are required. If not, the process 350 ends at block 368. If so, the process flows to block 366 where the gantry 50 is actuated so that the detector (e.g., 12) is positioned to a new angle of rotation and block 356 is then entered again with a new theta value.

At the completion of the process 350, a transmission map of the object is gathered using variable filters. This transmission map can then be utilized by the present invention to construct a set of nonuniform attenuation correction factors that can be used to correct image data gathered by the scintillation detectors during an emission study. The set of attenuation correction factors is used to compensating for the nonuniform attenuation of the emission radiation caused by the object's body.

IV. DUAL LINE SOURCE AND SLIDING DUAL TRANSMISSION DETECTION WINDOWS

An embodiment of the present invention is described for reducing the effects of side scatter (or cross-talk) during transmission and emission scanning in a dual scintillation detector environment. The present invention embodiment also operates within the above system wherein transmission and emission data are collected simultaneously. In this embodiment of the present invention, two sliding transmission detection windows are utilized and move across the detector surfaces in conjunction with the two scanning line source assemblies 20 and 22 (also called scanning line sources). The transmission detection windows are electronically generated and are used to define a particular area within the field of view of a detector. In all discussions to follow within this embodiment of the present invention, it is assumed that each detector (e.g., detector 10 and 12) is collimated and further that this embodiment of the present invention can be implemented within a gamma camera performing (1) simultaneous or (2) sequential emission/transmission scanning.

The two line sources and the two sliding windows move in synchronization to scan the field of view of the detectors and at any given position are all located within a single spatial plane (e.g., the long axis of the two line sources and the length of the two transmission detection windows are aligned within a single spatial plane). This spatial plane is transverse to the long axis of the object or patient being scanned. Particularly, if considering the gamma camera arrangement of FIG. 1, this spatial plane is perpendicular to the axis that runs through the two gantry rings 50. Using this dual line source scanning configuration, cross talk or scattered radiation originating from a given line source is not detected as emission data by the detector that is not associated with the given line source (e.g., the detector that is not directly facing the line source). Secondarily, the effect of emission crosstalk is also reduced.

The sliding transmission detection windows defined within the field of view of the detectors 10 and 12 are programmed by the computer system 112 to detect only photons within the energy level of the transmission radiation; photons of the emission radiation level detected within the window are ignored by the camera system. The ability to electronically define a window region within a scintillation detector is well known in the art, for instance reference is made to U.S. Pat. No. 5,304,806, entitled, "Apparatus and Method for Automatic Tracking of a Zoomed Scan Area in a Medical Camera System," issued Apr. 19, 1994, and assigned to the assignee of the present invention, which discusses tracking or "roving" zoom regions. As is known, a window region can be defined within and moved across the field of view of the detector and by acquisition processing, certain data detected by the scintillation detector within the window can be collected or ignored.

An illustration of the transverse orientation dual line source scanning and dual transmission detection window configuration of the present invention are shown in FIG. 10A, FIG. 10C and FIG. 10C. Detectors 10 and 12 are shown in a 90 degree configuration. Detector 10 is said to be associated with line source assembly 20 and detector 12 is said to be associated with line source assembly 22. There is a separate collimator 425 located in front of each detector 10 and 12 in order to collimate incoming photon radiation to the detector surface. As discussed above, each line source assembly 20 and 22 has its own collimating slit. A transmission window region 412 is defined within the field of view (FOV) of detector 12 and corresponds to line source assembly 22. This window region 412 spans the length of the field of view of detector 412 along the Y axis and in width (along X axis) is large enough to detect (and contain) the collimated transmission radiation emitted from line source assembly 22. The long axis of line source assembly 22, as discussed above, extends along the Y axis. Additionally, a second transmission window region 410 is defined within the field of view (FOV) of detector 10 and corresponds to line source assembly 20. This window region 410 spans the length of the field of view of detector 410 along the Z axis and in width (along X axis) is large enough to detect (and contain) the collimated transmission radiation emitted from line source assembly 20. The long axis of line source assembly 20, as discussed above, extends along the Z axis.

To gather transmission radiation, the line source assemblies 20 and 22 move along the X axis and scan an object with transmission radiation which is detected within the transmission detection windows of the detectors 10 and 12. As the line source assemblies move along the X axis in synchronization with each other, the associated transmission window regions 410 and 412 also move in synchronization along the X axis with their associated line source assembly.

The progression of the line source assemblies and transmission detection windows along the X axis is shown in FIG. 10A, FIG. 10B and FIG. 10C. In FIG. 10A, the two line sources 20, 22 and the two transmission detection windows 410, 412 are shown at a given (start) position along the X axis. In FIG. 10B, the two line sources and transmission detection windows are shown in a further (mid) x axis position. In FIG. 10C, the two line sources and transmission detection windows are shown in another (end) X axis position. Effectively, in electronics, the transmission detection windows 410, 412 are scanned across the detectors FOVs in synchronization with the line sources and create two spatial acceptance windows for acceptance of transmission data and rejection of photon radiation within the emission energy level. It is appreciated that a transmission scanning operation can also occur in the reverse direction across the detector's FOVs, e.g., from FIG. 10C to FIG. 10B to FIG. 10A.

It is appreciated that the computer system 112 (of FIG. 4) is programmed according to the present invention to define the transmission detection windows 410, 412 and to displace or scan them along the surface of the detectors 10 and 12 during a transmission scan. Defining a transmission detection window and scanning such along the field of view of a detector is well known in the art, for instance, as taught by Tan et al. in the reference entitled "A Scanning Line Source for Simultaneous Emission and Transmission Measurements in SPECT," cited above.

In this configuration, at any point along the x axis, the two line sources 20 and 22 and the two transmission detection windows 410 and 412 are located within the spatial YZ plane. Regardless of the position along the X axis of the transverse line source assembly of the present invention, the long axis of two scanning line sources 20 and 22 and the long axis of two transmission detection windows 410 and 412 remain within a single YZ spatial plane, for instance, refer to FIG. 10A, FIG. 10B, and FIG. 10C.

Under this configuration, the long axis of the dual line source assemblies and the dual transmission detection windows are within a spatial YZ plane that is perpendicular (transverse) to long axis of the object being scanned (e.g., assumed to along the X axis). Therefore, the configuration of the present invention is called a "transverse" transmission configuration.

During the scan session, transmission radiation is emitted from the line sources and this transmission radiation is detected by the scintillation detectors after passing through an object of interest. Simultaneously, emission radiation is emitted from the object and is detected by the detector. Within the present invention, the transmission radiation is utilized to create a nonuniform attenuation correction map of the object being scanned. Only transmission photons (e.g., photons detected within the transmission energy range) are detected within transmission detection windows 410 and 412. Emission photons (e.g., photons detected within the emission energy range) are ignored within the transmission detection window. Due to source and detector collimation and the configuration of the present invention, transmission photons are not detected outside the transmission detection windows 410 and 412. While transmission information is detected and collected within transmission detection windows 410 and 412, the remainder of the FOVs of the detectors detect and collect emission data.

FIG. 11A illustrates in manner in which the transverse configuration of the present invention effectively eliminates the effects of cross-scattering of transmission photons from contaminating the emission image. Essentially, line source collimation and detector collimation (within the configuration of the present invention) ensure that: (1) nonscattered transmission photons fall into the transmission detection window of an associated detector to the radiating line source; and (2) cross scattered transmission photons are detected in the transmission detection window of a detector that is not associated with the radiating line source (e.g., the orthogonal line source). For example, nonscattered transmission photons radiated by line source 20 are detected within transmission detection window 410 and scattered transmission photons radiated by line source 20 are detected within transmission detection window 412 and vice-versa for transmission photons emitted from line source 22. The above is true irrespective of the position of the line sources and transmission detection windows as they are scanned in synchronization along the X axis (which is into and out of the plane of FIG. 11A).

Various photon radiation sources can be used within the scope of the present invention. An exemplary implementation is the use of Tl-201 (at 100-keV) for the emission radiation source and Gd-153 (at 72-keV) as the transmission radiation source. FIG. 11A illustrates a cross section (in the YZ plane) of the detector configuration of the present invention. The present invention configuration rejects Gd scatter within the Tl transmission detection windows 410 and 412. A side view of sources 22 and 20 are shown and detectors 10 and 12 are shown in a 90 degree configuration. As discussed above, the detectors are each collimated.

A 100-keV transmission photon (Gd-153) is emitted from line source 22 along path 436, cross-scatters within the object 5 and is detected within nonassociated transmission detection window 410 (e.g., within the orthogonal detector). The detection window 410 is not associated with source 22 because transmission radiation emitted from line source 22 should be detected by the associated detection window 412 (e.g., absent photon scatter). Due to the configuration of the present invention, this cross scattering photon is forced to be detected within window 410, otherwise, it would have been absorbed by the detector's collimator and not detected at all by detector 10. There is no other location within detector 10 or detector 12 where the cross-scattering transmission photon can end up (assuming only one scatter event occurs) besides a transmission detection window.

The scattering within object 5 reduces the energy of the transmission photon, so it is detected within transmission detection window 410 at 72-keV (which is within the emission energy level). However, within the present invention, window 412 only responds to photons within the transmission energy level (e.g., within 100-keV). Therefore, this scattered transmission photon (having a Tl-201 count) is vetoed by the transmission detection window and not recorded by detector 10. Tl-201 photons detected elsewhere within the FOV of detector 10 are recorded as proper emission photons. It is appreciated that if the photon had cross scattered out of the (YZ) plane of FIG. 11A, due to collimation of the detector 10, the photon would not have been detected by detector 10. In addition, since the source 22 is collimated, nonscattered transmission photons are not detected outside window 412 of detector 12.

Shown by FIG. 11A, cross-scattering can also occur as a result of transmission radiation (100-keV) emitted from line source 20 shown by path 438. The transmission photon cross-scatters through object 5 and due to the configuration of the present invention the cross scattering photon is detected within nonassociated detection window 412. However, after scattering, the photon loses energy and becomes a 72-keV energy photon. Window 412 responds only to photons within the transmission energy level (100-keV in this example), therefore, this cross scattered photon is ignored. If the cross scattered photon did not remain within the YZ plane of FIG. 11A, it would have been stopped by the collimator of detector 12 and not detected at all. The remainder of the FOV of detector 12 is free to detect and collect emission radiation within the 72-keV energy level. Since the source 22 and detector 12 are collimated, nonscattered transmission photons are not detected outside window 412. Since the source 20 is collimated, nonscattered transmission photons are not detected outside window 410.

As a result of the present invention, cross scattering transmission photons are not allowed to fall within regions of any detector that are gathering emission data. This effectively eliminates the contamination of cross scattering transmission data within the emission image of a dual detector gamma camera. When a scattered transmission photon falls within a transmission detection window, the scatter photons are effectively eliminated by the data acquisition electronics of the present invention (e.g., circuit 120 or computer system 112) due to energy discrimination.

The emission image is free of cross-scatter contamination because the cross-scatter photons emitted from line sources 20 and 22 either: (1) fall within nonassociated detector regions 412 and 410 (respectively) and are therefore ignored; or (2) are absorbed by the detectors' collimators and are not detected at all. Further, transmission radiation (emitted by the line sources) that does not scatter is detected within associated transmission detection windows 410 and 412 and does not contaminate the emission image. Within the present invention, there is no need to perform additional measurements to estimate and subtract effects due to cross-scatter.

FIG. 11B illustrates the energy distribution of detected photons resultant from the configuration of FIG. 11A. As shown in FIG. 11B, the shaded area 404 represents the emission Gd photopeak plus the scatter radiation. As shown, the scatter distribution tails into the transmission Tl window. Also shown is the Tl photopeak distribution 403.

An implementation of the present invention is shown in FIG. 12A wherein the scanning line source system effectively rejects Tl scatter in a Gd window within a system using Tl-201 (at 167-keV) as emission photons and Gd-153 (at 100-keV) is used for transmission. In this configuration, the effects of emission cross-talk are reduced. The resultant Gd transmission image is effectively free of emission cross-scatter contamination. For example, an emission photon may scatter of off the object 5 following in path 434 and lose energy. The emission photon will then fall within transmission detection window 410 and will have an energy level of a transmission 100-keV photon. However, the transmission Gd count rate inside the detection window 410 overwhelms the downscatter from the 167-keV emission cross scatter. The line source collimation and detector collimation ensure that nonscattered transmission radiation falls into the transmission detection window of its associated detector. Gd counts occurring inside the transmission detection windows are accepted and Gd counts outside moving transmission detection windows are rejected because source collimation means no valid Gd photons are outside of the transmission detection windows.

FIG. 12B illustrates the energy distribution of detected photons resultant from the configuration of FIG. 12A. As shown in FIG. 12B, the shaded area 402 represents the Tl photopeak plus the scatter radiation. As shown, the scatter distribution tails into the transmission Gd window. Also shown in the Gd photopeak distribution 401.

FIG. 13A and FIG. 13B illustrate that the transverse transmission detection window configuration of the present invention is advantageous for reducing cross-scatter wherein an axial orientation of the transmission detection windows is not. Axial orientation means that the long axis of the detection window and the long axis of the patient are along the X axis. FIG. 13A illustrates the present invention configuration wherein the long axis of the line sources and transmission detection windows are oriented transverse with respect to the patient. FIG. 13B illustrates the present invention configuration wherein the long axis of the line sources and transmission detection windows are oriented axial with respect to the patient. For both configurations, an exemplary implementation is the use of Tl-201 for the emission radiation source and Gd-153 as the transmission radiation source.

For example, FIG. 13A illustrates a cross section of the present invention transmission configuration that is sliced along the transmission detection windows in the YZ plane. Within the present invention, the long axis of the line sources and transmission detection windows are oriented transverse to the object (e.g., perpendicular to the X axis). As before, detectors 12 and 10 are at right angles and windows 412 and 410 extend along the detector surfaces due to the orientation of the cross section. A transmission photon is emitted from line source 22, along path 482 and is scattered within the plane of FIG. 13A and is detected within window 410 of detector 10. As discussed previously, it will be excluded from the transmission data because transmission detection window 410 only responds to transmission energy level photons.

However, assume the long axis of the transmission detection windows were oriented axial to the object (e.g., along the X axis). The cross sectional view of FIG. 13B (within the YZ plane) illustrates once again that detectors 10 and 12 are at 90 degree orientation, but the cross section of transmission detection window associated with detector 12 is displayed as area 472. The cross section of transmission detection window associated with detector 10 is shown as 474. The long axis of these transmission detection windows 472 and 474 extends out of and into the page of FIG. 13B. Also, in this cross section, line source 22 appears as a circle as shown. Assuming a transmission photon taking path 484 cross scatters from object 5, it can land on detector 10, but it is not guaranteed to land within transmission detection window 474. As shown in FIG. 13B, the cross scatter photon lands within the emission recording portion of the FOV of detector 10. In this case, the transmission photon will be improperly detected as a emission photon because the energy loss from the photon due to the scatter will reduce its energy level to that of the emission energy level. Therefore, using traverse scanning line sources and traverse oriented moving transmission detection windows, the cross scatter contamination is not eliminated within the axial oriented transmission detection windows. This is one reason why the present invention utilizes transverse scanning line sources and transverse oriented moving transmission detection windows, in this way, the cross scatter contamination is effectively eliminated.

The present invention transverse dual transmission line source scanning configuration is used to collect uncontaminated transmission data (e.g., free from cross-scatter contamination). The transmission data or "counts" collected by the present invention are stored in a computer memory, such as memory 102 of computer system 112 (see FIG. 4). Using well known procedures, the transmission data is converted into nonuniform attenuation correction factors by the computer processor 101. These nonuniform attenuation correction factors are also stored in a computer memory, such as memory 102 or even 104 of FIG. 4. As discussed previously, the nonuniform attenuation correction factors are used by the computer processor 101 in well known procedures to correct collected emission data from the gamma camera system to compensate for nonuniform attenuation from the scanned object.

A. Combination With Zoom Tracking

An embodiment of the transverse dual sliding detection window and dual transmission line source system of the present invention is advantageously utilized in conjunction with zoom tracking windows that allow detailed images of a particular organ of interest (e.g., such as in cardiac studies). The details of the zoom tracking implementation within a dual detector system are described in U.S. Pat. No. 5,304,806, entitled, "Apparatus and Method for Automatic Tracking of a Zoomed Scan Area in a Medical Camera System," issued Apr. 19, 1994, and assigned to the assignee of the present invention. According to this disclosure, a special zoom window (or region) is defined within the FOV for each detector within the detector electronics and/or computer system's data acquisition processes. This window is defined to cover the field of view of the detector which coincides with a particular organ of an imaged patient, e.g., the heart. The detector electronics provide for an image magnification for emission radiation that are detected within the zoom windows.

As the detectors traverse about the object under ECT movement, the zoom windows displace ("rove") relative to the surface of the detectors so that the heart (or other organ of interest) remains centered and within the FOV of each zoom window. In effect, the zoom windows track the heart for each ECT rotation angle. These zoom windows detect emission radiation from the tracked organ (e.g., heart). Since the zoom windows are smaller than the entire FOV of a detector, the image rendering capacity of the gamma camera can be focused on the zoom window and the resultant image generation quality is increased (e.g., resolution is increased). In effect, the size of the pixels defined within the zoom window can be decreased relative to their full FOV size.

FIG. 14A illustrates that zoom tracking is implemented in conjunction with the transverse dual detector transmission window and dual line source scanning configuration of the present invention. In such case, the zoom windows 452 and 454 are defined on the surface of the detectors and move up and down as shown by the arrows 452a and 454a in order to track an object of interest as the detectors 10 and 12 undergo ECT rotation about the object. It is appreciated that for any given angle, the zoom windows remain fixed and rove only between angles. In an exemplary configuration, the FOV of a particular detector is roughly 51×31 cm in area and a particular zoom window can be 30×30 cm or 38×38 cm in area. The detectors 10 and 12 electronically collect emission data (e.g., counts) only within the zoom regions 452 and 454 for each angle of rotation. It is appreciated that the entire FOV of the detector 10 and 12 may be detecting emission radiation, however, only that emission radiation that is detected within the zoom windows (regions) is stored and used for image reconstruction.

According to this aspect of the present invention, simultaneous with the collection of emission data within the two roving zoom windows, transmission data is also collected within the scanning transmission detection windows 410 and 412. An exemplary implementation is the use of Tl-201 for the emission radiation source and Gd-153 as the transmission radiation source. Although not shown in FIG. 14A, two scanning line sources are also present and move in synchronization with the two transmission detection windows, as discussed previously. For each angle of rotation, the transverse transmission detection windows scan across the FOV of the detector according to arrows 412a and 410a as discussed above in order to collect transmission data. For each angle or rotation, the zoom windows 452 and 454 assume a new spatial position (rove) to track the object of interest. However, unlike the scanning transmission detection windows 412 and 410, at any given angle of rotation the zoom windows 452 and 44 remain fixed until the next angle of rotation is entered.

The transmission detection windows 410 and 412 of the present invention report only photons within the transmission energy level and reject other detected photons, e.g., emission energy level photons which result from: (1) scattered transmission photons; and (2) nonscattered emission photons. The zoom regions 452 and 454 report emission photons because the collimation of the line sources and the detector provides that no valid transmission data should fall outside the two transmission detection windows 410 and 412.

It is possible, as shown in FIG. 14A, for the transmission detection windows 410 and 412, as they scan across the FOV of their associated detectors, to partially coincide with the zoom windows 452 and 454. When this happens, an area of the zoom windows (e.g., 452b and 454b) that overlaps with the transmission detection windows act as a transmission detection window and acts to reject photons of the emission energy level. In effect, regions 452b and region 454b collect transmission energy level photons and rejects emission photons. However, this state is temporary as the transmission detection windows are moving across the FOV of the scintillation detectors.

Figure 14B:
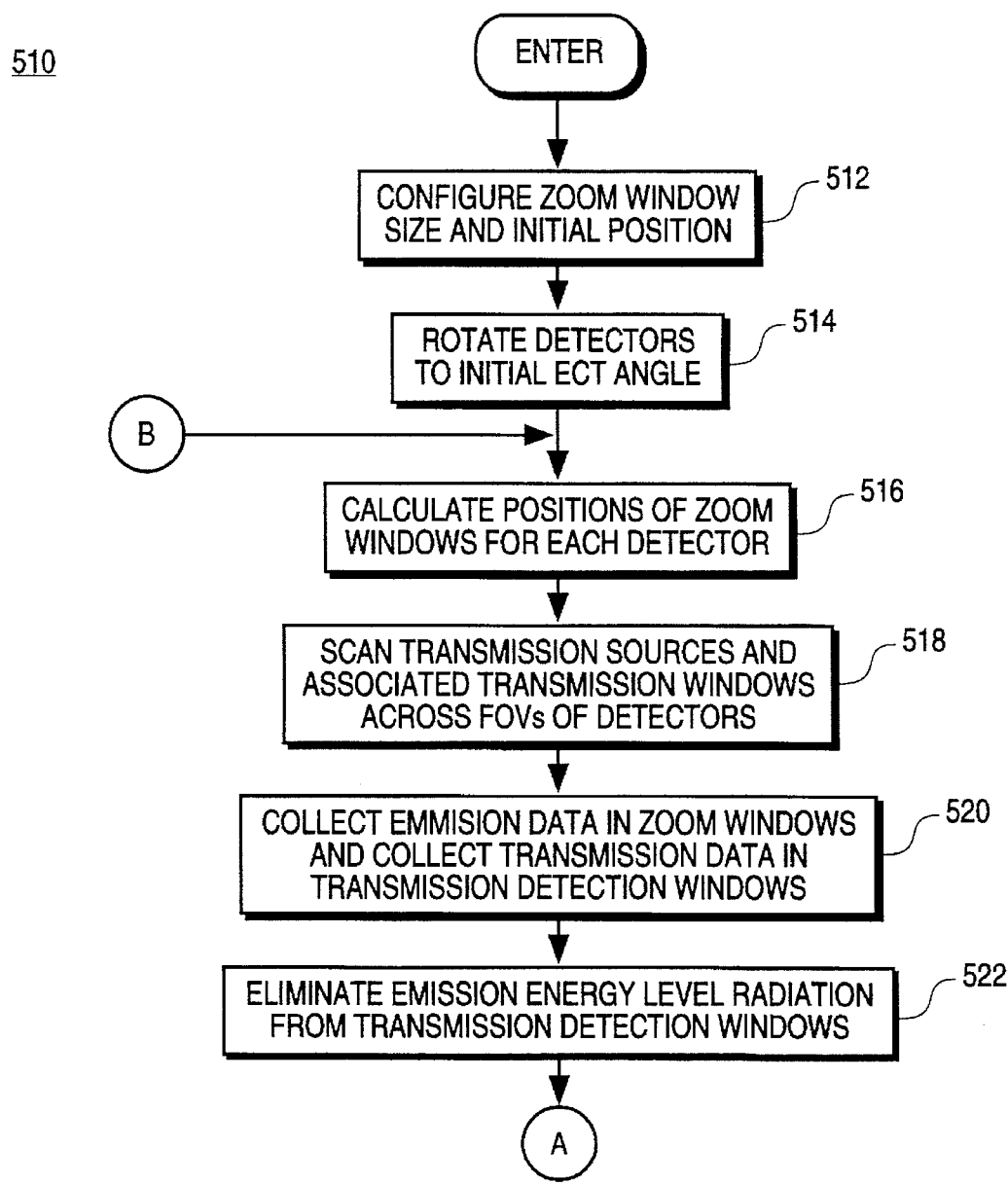
FIG. 14B and FIG. 14C illustrate an operational flow diagram of the tracking zoom region and scanning transmission detection window embodiment of the present invention.
Figure 14C:
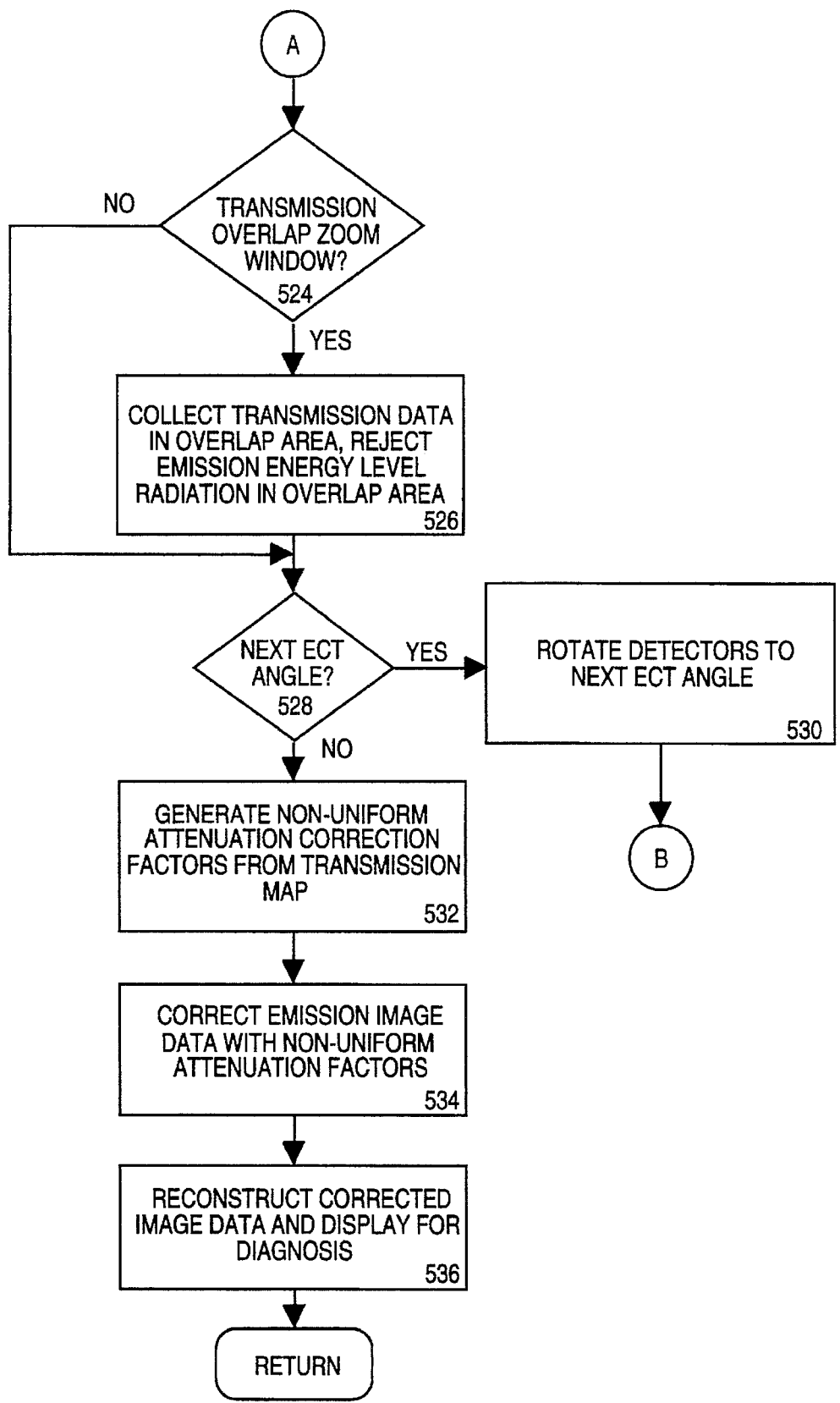

FIG. 14B and FIG. 14C illustrates a flow diagram of the processing tasks 510 performed by the scanning transmission line source embodiment of the present invention used in conjunction with roving zoom tracking windows. An exemplary implementation is the use of TI-201 for the emission radiation source and Gd-153 as the transmission radiation source. The processing starts at block 512 in which the patient is placed in the gamma camera system (e.g., such as the one shown in FIG. 1) and the gamma camera is initially configured and initialized. The two detectors 10 and 12 are oriented at a 90 degree angle about the patient. At block 512, the zoom regions are initially defined in terms of size and initial placement in order to locate the object of interest (e.g., the heart); this can be accomplished according to the procedure and mechanisms described in U.S. Pat. No. 5,304,806 (cited above). At block 514, if not already at the starting angle, the detectors are rotated by the gantry structure to the first angle for the ECT study. At block 516, the positions of the zoom windows (regions) are computed for each detector for the initial rotation angle; this can be accomplished according to the procedure and mechanisms described in U.S. Pat. No. 5,304,806.

At block 518, the two scanning line source assemblies 20 and 22 scan across the FOV of each detector to irradiate the patient and their associated transmission detection windows scan in synchronization with the associated line source; this process is accomplishing using the configuration shown in FIG. 10A, FIG. 10B, and FIG. 10C. Although programmable, an exemplary scan speed is 1 cm/sec for the configuration. It is appreciated that a scan speed computation (as described above based on a prescan duration) can be performed during this step in order to reduce the radiation exposure amount for the patient.

Block 520 occurs simultaneously with block 518. At block 520, the present invention detects and reports transmission energy level photons (100-keV) within the transmission detection windows (e.g., 410 and 412). Simultaneously, emission energy level photons (e.g., 72-keV) are detected and reported within the roving zoom regions (e.g., 452 and 454), but transmission energy level photons are rejected (or not detected at all due to collimation of the source and the detectors) within the roving zoom regions.

At block 522, emission energy level photons (e.g., 72-keV) are rejected within the transmission detection windows 410 and 412 (e.g., they can be a result of cross-scatter). Cross-scatter transmission photons are eliminated during this step. It is appreciated that block 522 is performed simultaneously with block 520. At block 524, the present invention checks if any part of the transmission detection windows overlap with a zoom window as the transmission detection windows scan across the FOV of the detector surfaces. If so, then at block 526, transmission energy level photons are detected and reported in the overlap area and emission energy level photons are rejected within the overlap area; in effect, the overlap is treated as purely a part of the transmission detection windows. Processing then flows to block 528. At block 524, if no overlap, then processing flows to block 528. It is appreciated that block 524 and block 526 can effectively occur simultaneously with block 522.

At block 528, the transmission and emission scanning operations for a given ECT angle are completed and the proper transmission and emission image data is stored in computer system 112. If another ECT angle of rotation is required (e.g., the ECT session is not complete), then at block 530, the gantry structure rotates the detectors 10 and 12 to a new angle of rotation and block 516 is once again entered.

If the ECT rotation angles are complete, then the ECT data acquisition session is over. At block 532, a nonuniform attenuation correction map is generated based on the transmission data collected for each ECT angle of rotation. At block 534, the emission data is corrected utilizing well known correction factors (e.g., for linearity and energy) including the nonuniform attenuation correction map generated by block 534 to correct for nonuniform attenuation of the patient's body. At block 536, the present invention then reconstructs the corrected emission data (using well known reconstruction procedures) and displays the reconstructed data as required for diagnosis.

V. LFOV TRANSMISSION ACQUISITION USING SFOV EMISSION ACQUISITION

The present invention also includes an embodiment directed at eliminating truncation associated with the reconstruction of transmission information as done in prior art systems. Transmission image information truncation results when a field of view smaller than that required to image the entire body is used to collect transmission information. Emission information is also collected with this small field of view (SFOV). The result is higher resolution for the emission data but transmission data truncation results because not all of the body was scanned during the transmission scan. Special algorithms are then needed to anticipate the transmission data in those areas of the body that were not directly scanned. Body contour information is used to supplement the transmission data.

The present invention utilizes a large field of view scintillation detector (e.g., 20"×15") and therefore is able to collect transmission data using a large field of view acquisition (LFOV) scan. However, in order to increase image quality when imaging a small organ (e.g., the heart), the present invention allows emission data to be collected using a roving zoom region having a small field of view. Use of a roving zoom region for emission data acquisition within the present invention analogous to the technique described in detail within U.S. Pat. No. 5,304,806, entitled, "Apparatus and Method for Automatic Tracking of a Zoomed Scan Area in a Medical Camera System," issued Apr. 19, 1994.

Since a LFOV transmission scan is acquired the whole body is scanned and no transmission truncation is required. Further, since a SFOV emission window is used, the image quality of the resulting emission image is high. Further, since no transmission truncation is performed, the approximations and corrections performed by the prior art (e.g. in order to anticipate the transmission data not gathered by a SFOV transmission scan) are not required. As such, the present invention offers the advantageous results of providing a complete and accurate transmission map (e.g., nonuniform attenuation correction map) in addition to a high quality emission image.

Because the present invention utilizes a LFOV transmission acquisition scan and a SFOV emission acquisition scan, the pixel sizes between the transmission and the emission data are different since, generally, the number of pixels with a transmission or emission scan is constant. Namely, the pixel sizes with respect to the transmission scan are larger than the pixel sizes with respect to the emissions scan. Although many different matrix sizes can be utilized within the scope and spirit of the present invention, a particular and exemplary size is illustrated for discussion only. For example, the present invention can utilize a 64×64 imaging matrix to cover the full field of view of the detector (e.g., 20"×15") for the transmission scanning. The present invention an also utilize a 64×64 imaging matrix to cover a small field of view (e.g. for cardiac studies) to encompass a particular organ of interest (e.g., the heart) over an imaging area of 10"×10" or 15"×15", for instance.

As can be seen, the pixel sizes for the emission data acquisition are smaller than the transmission acquisition and therefore offer more resolution for imaging the organ of interest. The SFOV emission window is the roving zoom window or region referred to in U.S. Pat. No. 5,304,806. Because the pixels are smaller within the zoom region the emission image appears larger and therefore "zoomed." Further, the zoom region is called a "roving" zoom region because (as discussed above) during ECT rotation, the region or window will displace relative to the surface of the scintillation detector in order to track the organ of interest within its field of view as the scintillation detector rotates about the body.

It is appreciated that for a tomographic reconstruction, the images taken at each rotation or ECT angle assume a fixed center of rotation and further that the objects imaged are steady with respect to that center of rotation. However, with respect to a roving zoom region, since the emission acquisition window displaces relative to the detector surface to track an organ, effectively the emission tomogram has a "virtual" center of rotation in that the imaged organ becomes the "virtual" center of rotation. Further, this "virtual" center of rotation may not be the same as the actual physical center of rotation defined by the gantry 50 and detector mechanisms. It is appreciated that if the imaged organ is at the physical center of rotation then the zoom region would not need to rove at all.

Within the present invention embodiment that allows the emission acquisition to be imaged through a roving zoom region of the detector surface, the transmission acquisition data (which is taken simultaneously) is spatially shifted or corrected to account for the "virtual" center of rotation defined by the imaged organ. Namely, as the roving zoom region displaces a given amount for a given angle of rotation (e.g., to track the "virtual" center of rotation), the transmission data collected for that angle will too be shifted or corrected to account for this displacement from the true center of rotation. In this way, during reconstruction of both the transmission and the emission data, like parts of the same body are reconstructed in the same position. The attenuation correction map will spatially match up or align with the emission reconstruction map.

In addition, since the transmission pixels are larger than the emission pixels, generally, the present invention also performs a form of linear interpolation of the transmission data in order to generate transmission pixels of the same size as the emission pixels. Again, this is done so that the resolution between the transmission map and emission data are the same in order to properly correct the emission data.

Figure 15A:
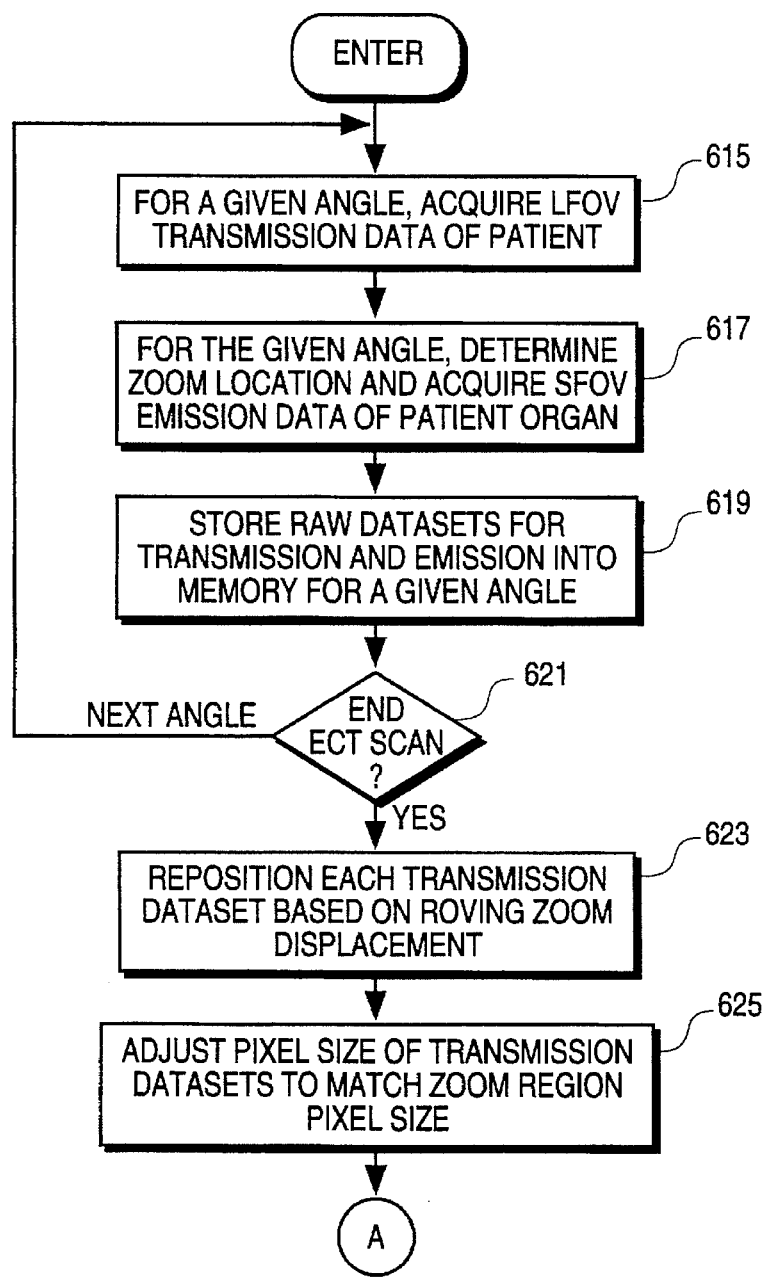
FIG. 15A and FIG. 15B illustrate a process flow diagram of tasks executed by the present invention for LFOV transmission image acquisition and SFOV emission image acquisition.
Figure 15B:
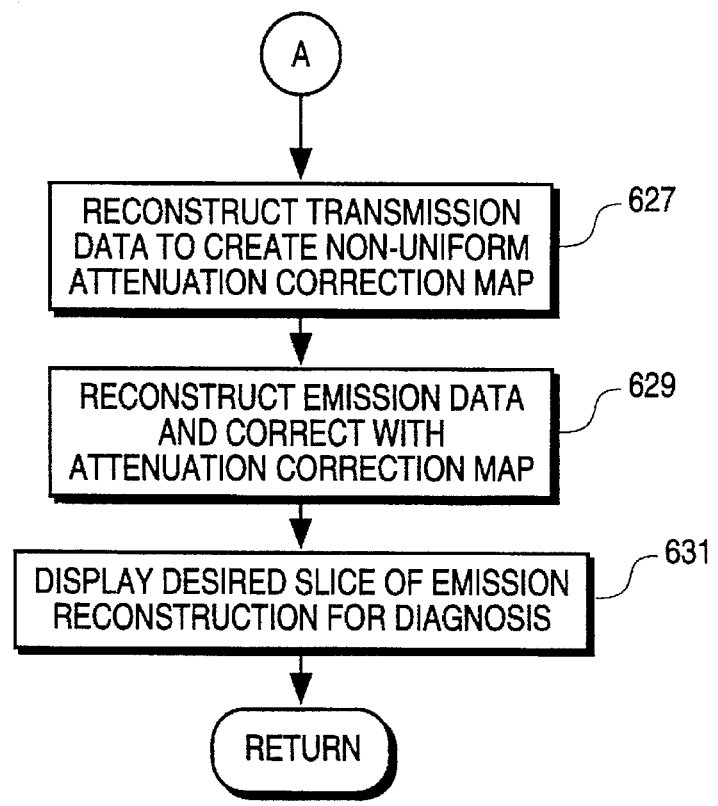

FIG. 15A and FIG. 15B illustrate a processing diagram of the procedure 610 utilized by the present invention to perform LFOV transmission scan with a SFOV emission scan. It is appreciated that the computer system 112 performs many of the tasks as will be described hereinafter apart from the actual data acquisition steps performed by the scintillation detectors 10 and 12 and the signal processing acquisition hardware 120. It is appreciated that the process 610 can be employed for both a single detector and for a dual detector configuration. However, the implementation with a dual detector is described below for illustration. The implementation within a single detector system is a readily determinable from the dual detector process.

To perform LFOV transmission with SFOV emission, the process 610 is entered and at block 615 the gantry is positioned at an initial ECT angle for the scan. Detectors 10 and 12 are oriented at 90 degrees to each other. For this ECT angle, a transmission scan is performed on the entire body using the line sources 20 and 22 and imaging information is recorded (e.g., transmission data) across the full field of view of the detectors 10 and 12. It is appreciated that a scan speed determination can be performed at this step 615 to reduce the transmission radiation exposure to the patient. Namely, a prescan can be performed followed by the transmission scan of a minimum duration of time. The transmission acquisition is then based on a LFOV because is it based on the entire field of view of the detector (for example 20"×15"). An exemplary matrix size acquisition for transmission information is 64×64 pixels (per detector), but is programmable.

It is appreciated that the transmission scan of block 615 may also include the use of a variable filter assembly 22 as shown in FIG. 8C in order to reduce count density in unobstructed portions of the detector. In such case, the computer system obtains a body contour of the object and then selects the proper filter for use.

At block 617 of FIG. 15A, at the initial ECT angle, the proper initial positions of the roving zoom windows (e.g., with respect to the scintillation detectors) are determined as described in U.S. Pat. No. 5,304,806. Also, the proper sizes of the roving zoom windows are selected which determines the amount of magnification utilized. Exemplary sizes for the emission windows are 10"×10" and 15"×15", but these are programmable. At block 617, emission data is obtained from the detectors 10, 12 only from the roving zoom window regions of each detector. It is appreciated that the transmission data acquisition of block 615 and the emission data acquisition of block 617 can occur simultaneously. Further, it is appreciated that the above described method for eliminating cross-talk can be utilized by this implementation of the present invention at blocks 615 and 617, as appropriate. The emission acquisition is then based on a SFOV since is relates only to the data acquired via the roving zoom regions. An exemplary matrix size acquisition for emission information is 64×64 (per detector) pixels but is programmable.

Figure 16A:
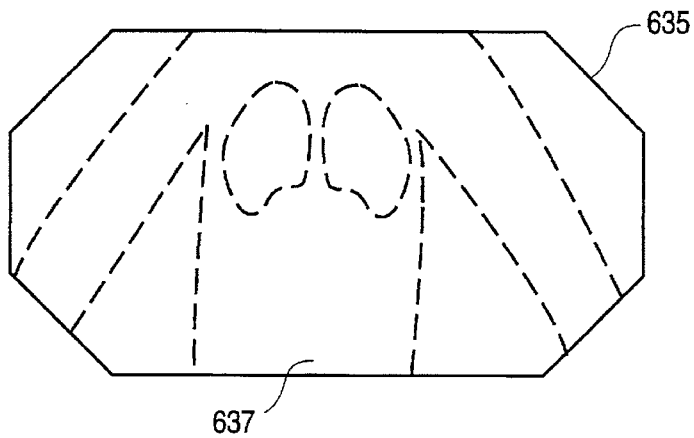
FIG. 16A and FIG. 16B illustrate the present invention step of adjusting transmission data according to a spatial position of a roving zoom region used for emission scanning.
Figure 16B:
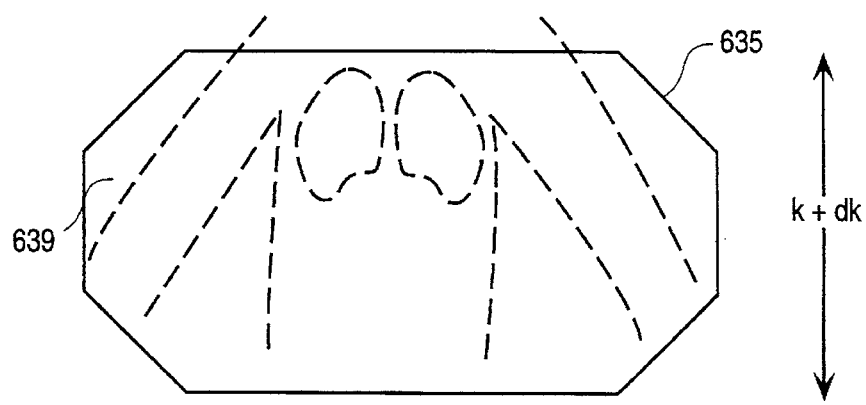
Figure 16C:
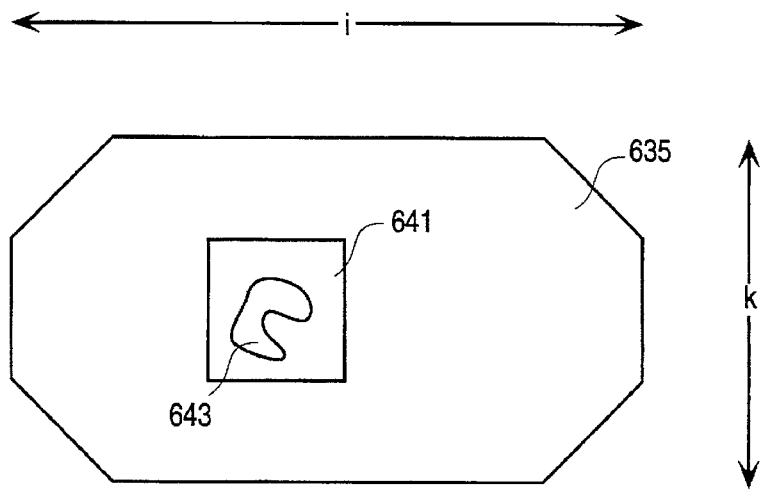
FIG. 16C and FIG. 16D illustrate the present invention use of roving zoom regions for emission scanning.
Figure 16D:
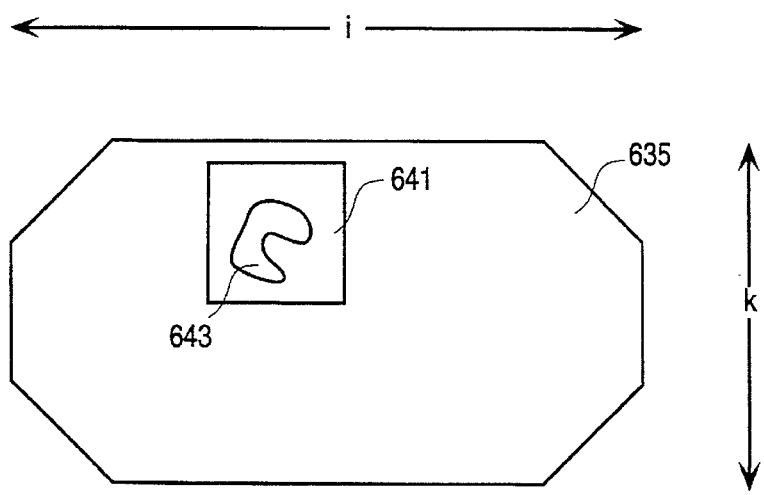

FIG. 16C and FIG. 16D illustrate movement of the roving zoom window during emission scanning. FIG. 16C illustrates the roving zoom window 641 located at an initial position (i, k) within the field of view 635 of a detector 10. An image of the heart 643 is displayed. FIG. 16D illustrates the same configuration at a different ECT angle. The roving zoom region 641 has displaced by some di and dk value. As shown, the roving zoom region 641 has been displaced upward to track the heart so that the image of the heart 643 remains in the field of view of the zoom region for each ECT rotation angle. At the completion of the ECT scan, there is a different displacement (di and dk) for each roving zoom region for each angle of rotation (theta). For example, there is a di(theta) and dk(theta) for the roving zoom region for detector 10 and for detector 12. These are stored in memory. The following dataset can be generated in memory:

| ECT Angle | Detector 10 | Detector 12 |
| --- | --- | --- |
| theta0 | di(theta0), dk(theta0) | di(theta0), dk(theta0) |
| theta1 | di(theta1), dk(theta1) | di(theta1), dk(theta1) |
| theta2 | di(theta2), dk(theta2) | di(theta2), dk(theta2) |
| theta3 | di(theta3), dk(theta3) | di(theta3), dk(theta3) |
| theta4 | di(theta4), dk(theta4) | di(theta4), dk(theta4) |
| . | . | . |
| . | . | . |
| . | . | . |
| thetan | di(thetan), dk(thetan) | di(thetan), dk(thetan) |

Refer to FIG. 15A. After a predetermined imaging duration wherein sufficient transmission and emission counts are obtained, at block 619, the present invention then stores the emission image counts as a dataset matrix into a memory device and references this information by the current ECT angle. Also at block 619, the present invention stores the transmission image counts as a dataset matrix into a memory device and references this information by the current ECT angle. At block 621, the present invention then determines if the ECT scan is complete. If not, then a new angle of rotation is determined and the gantry structure 50 is positioned such that the detectors 10 and 12 are properly rotated to the new angle. Processing then returns to block 615 so that the image dataset matrices for the transmission scan and for the emission scan can be completed and stored for this new ECT angle.

At block 621, if the scanning for the last ECT angle is complete, then processing continues to block 623 where the transmission dataset matrices for each detector and for each ECT angle are spatially corrected to account for the virtual center of rotation defined by the roving zoom region. In effect, the roving zoom regions, by moving across the field of view of the detectors to track the organ of interest, act to create virtual center of rotation that is different from the actual center of rotation of the gantry structure. The virtual center of rotation centers the target of interest (e.g., the heart in cardiac scans). However, the transmission information LFOV does not adjust spatially (e.g., rove) during the ECT scan because this is a full field of view scan which is based on the actual center of rotation of the gantry. Therefore, the transmission information is acquired based on the center of rotation of the gantry and the emission data is gathered based on the virtual center of rotation. For proper application of the transmission image data to the emission image data, after tomographic reconstruction, their data must be based on a similar center of rotation.

At block 621 of FIG. 15A, the transmission data is adjusted or compensated so that it is becomes based on the virtual center of rotation so that the transmission data and the emission data match for a proper reconstruction. Therefore, for each angle (theta) the transmission dataset matrix is offset spatially according to the amount of displacement of the roving zoom region for that angle theta (e.g., by di(theta), dk(theta)). An illustration of this effect is shown in FIG. 16A and FIG. 16B for a given angle of rotation. FIG. 16A illustrates the dataset matrix for a transmission scan of detector 10 without compensation. FIG. 16B illustrates that this raw transmission data is offset by di and dk for a given angle theta to account for the roving zoom motion. By performing the compensation for each dataset matrix of each detector for each angle, theta, the present invention effectively translates the transmission data so that it becomes based on the virtual center of rotation (e.g., the organ) and not the gantry center of rotation. After the repositioning of block 621 is complete, the transmission data matrices are stored in memory.

At block 625 of FIG. 15A, the present invention adjusts the pixel size of the transmission dataset matrices to match the zoom region pixel size. For instance, assuming the zoom region pixels are at some magnification M, larger than 1.0 (e.g., 1.5 magnification), then the pixels of the transmission scans are reduced in size and increased in number by the present invention and interpolated using a linear interpolation procedure until the pixel sizes between the transmission and the emission scan match. For example, assume the transmission dataset matrices are acquired in matrix sizes of 64×64. The present invention transforms this matrix onto a larger matrix dataset (e.g., 128×128) which effectively reduces the size of the individual pixels of the transmission dataset matrices but increases their number. However, since the magnification of the emission data (e.g., M) can be less than twice magnification, the new transmission matrix may not be completely filled.

Figure 17:
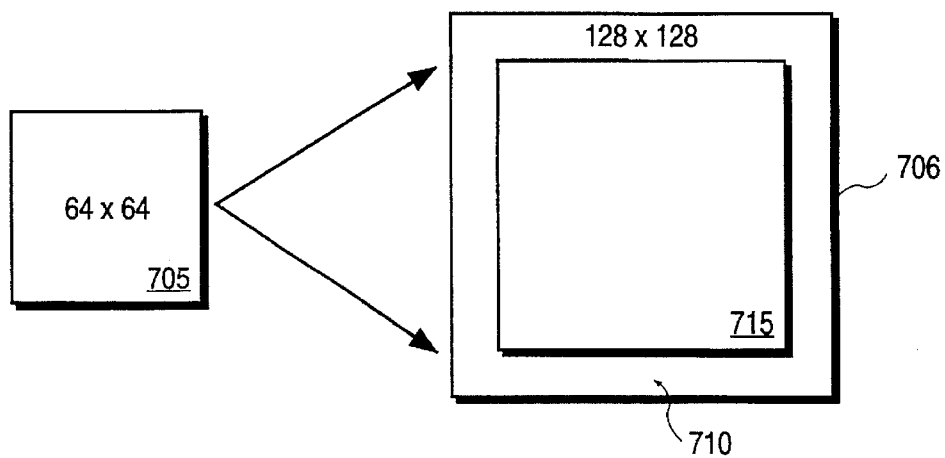
FIG. 17 illustrates a transformation performed by the present invention to adjust the pixel size of the transmission dataset matrices to match the pixel size of the emission dataset matrices.

Refer to FIG. 17 for an illustration. An exemplary transmission dataset matrix is shown as 705 (composed of a matrix of 64×64 pixels). The image data of the matrix 705 is transformed by the present invention into a larger matrix 706 (composed of a matrix of 128×128 for example). The transmission image data from matrix 705 is recorded into area 715 and the boarder 710 is empty for cases where the zoom magnification (M) is less than 2. If, for example, the zoom magnification was 1.5, then each pixel within matrix 705 would be linear interpolated with its neighboring pixels wherein two adjacent pixels would create additional pixels in between, and so on, until the region 715 was complete and the transmission data was adjusted to the 1.5 zoom magnification. However, since matrix 706 is twice as large in both dimensions as matrix 705 and since M=1.5, the border 710 of the matrix 706 remains empty of valid data.

It is appreciated that there are a number of different techniques for transforming one image from a first matrix 705 to a second matrix 706 that contains more pixels of a smaller size, individually, as compared to the first matrix. Any of a number of well known methods may be performed consistent within the scope of the present invention. The important aspect of step 625 of FIG. 15A is that the pixel size of the transmission image information is adjusted to match that of the emission image information. Step 625 is done for each transmission dataset matrix for each detector for each angle of rotation and the results are stored in memory.

Process 610 of the present invention continues with FIG. 15B step 627 where the present invention performs a reconstruction of the transmission information to create a nonuniform attenuation correction map. It is appreciated that the processes and procedures for reconstructing image information taken at different ECT angles is well known. Any of a number of different and well known reconstruction procedures can be used consistent within the scope of the present invention. As an exemplary procedure, the present invention performs the maximum likelihood and expectation maximization iterative (MLEM) process for transmission reconstruction. According to the MLEM process, each transmission data set from each detector for each angle of rotation (e.g., after being corrected for roving zoom displacement and pixel size) is recalled from memory and used to generate the transmission reconstruction map. The transmission reconstruction can be performed a number of different ways, however, under an embodiment of the present invention it is performed across slices and the reconstruction image is stored in memory. During step 627, the reconstruction of the transmission data does not involve truncation, as done in the prior art, since a transmission scan using a LFOV was acquired.

The present invention then at step 629 performs the emission reconstruction using the emission data collected via the roving zoom region for each detector for each angle of rotation. During the reconstruction (e.g., using the MLEM process), the transmission reconstruction map is applied using well known procedures to correct for nonuniform attenuation of the body. Since the transmission reconstruction was corrected for roving zoom displacement (e.g., step 623) and corrected for pixel size (e.g., step 625), the transmission reconstruction can be directly applied to the emission reconstruction as a nonuniform attenuation correction map. The emission reconstruction/correction can be performed a number of different ways, however, under one embodiment of the present invention it is perform on a slice by slice basis and the reconstruction image is stored in memory.

At the completion of step 629, a reconstruction of the organ of interest is generated that has been corrected for nonuniform attenuation of the body. This reconstruction is of a high image quality because a SFOV emission scan was acquired using relatively small pixel sizes. Further, since the transmission scan was acquired under a LFOV, no errors due to transmission truncation were contributed by the present invention. Therefore, the emission image is of a higher quality because it was more accurately corrected for nonuniform attenuation by the complete transmission reconstruction of step 627.

At block 631 of FIG. 15B, the present invention then allows different "slices" through the emission reconstruction image to be displayed (e.g., on a CRT, printer, hardcopy device, disk drive storage, etc.) for diagnostic purposes and different slices may be selected and displayed via user input, as is well known.

It is appreciated that the flow 610 of the present invention has been described herein as providing the various fields of view (e.g., LFOV and SFOV) during the acquisition or "front end" processing of the present invention. Then, after acquisition, this information is processed by the computer system as described above. However, in certain circumstances, the application of certain fields of view can be performed at the processing side or "back end." In other words, some detector systems provide a maximum resolution of 4096×4096 for each detector head. The present invention can also be implemented by acquiring the totality of the possible data from each detector (assuming adequate storage and processing speed are provided) and then applying the field of views to this data electronically by discarding some of the acquired data for processing and binning the remainder of the image data to fit the particular pixel size desired.

It is appreciated that implementations of the present invention that apply the fields of view as described in the present invention (LFOV for transmission and SFOV for emission) at the "back end" processing stages are within the scope of the present invention as described herein.

The preferred embodiment of the present invention, a gamma camera system providing improved image generation via nonuniform attenuation correction maps, is thus described. While the present invention has been described in particular embodiments, it should be appreciated that the present invention should not be construed as limited by such embodiments, but rather construed according to the below claims.

What is claimed is:

1. An apparatus for collecting transmission data associated with an object, said apparatus comprising:
   a radiation detector for detecting radiation and reporting image information;
   a source of radiation for emitting transmission radiation through said object to said radiation detector;
   a processor coupled to receive information from said radiation detector and coupled to control said source of radiation, said processor for controlling said source of radiation to perform a first transmission prescan over said object for a first duration and generating in response thereto a first count density information;
   said processor for computing a second duration for a second transmission scan phase based on said first count density information; and
   said processor for controlling said source of radiation to perform said second transmission scan phase over said object for said second duration and generating in response thereto a second count density information.

2. An apparatus as described in claim 1 wherein said source of radiation is a scanning line source.

3. An apparatus as described in claim 1 wherein said radiation detector is a scintillation detector of a gamma camera.

4. An apparatus as described in claim 1 wherein said radiation detector is a pair of scintillation detectors and wherein said source of radiation is a pair of scanning line sources each configured to provide transmission radiation for a particular scintillation detector.

5. An apparatus as described in claim 1 further comprising a memory unit coupled to store and provide access to said first and said second count density information.

6. An apparatus as described in claim 1 wherein said processor is for computing a set of attenuation correction factors based on said second count density information, said set of attenuation correction factors used for correcting image data gathered by emission scanning of said radiation detector.

7. An apparatus as described in claim 1 wherein said second count density information is a distribution over different portions of said object and wherein said processor is for inputting a minimum count density, wherein said distribution contains at least said minimum count density for each portion of said object.

8. An apparatus as described in claim 7 wherein said processor is for analyzing said first count density information and determining a minimum observed count density in response thereto, wherein said minimum observed count density corresponds to a portion of said object exhibiting maximum attenuation.

9. An apparatus as described in claim 8 wherein said processor determines said second duration according to the procedure:

$$Ts = Co \frac{Tp}{Cm}$$

wherein Ts is said second duration, Cm is said minimum observed count density, Tp is said first duration, and Co is said minimum count density.

10. An apparatus for collecting transmission data associated with an object, said apparatus comprising:
   a scintillation detector for receiving radiation and reporting image information;
   a line source of radiation for emitting transmission radiation through said object to said scintillation detector;
   a processor coupled to receive information from said scintillation detector and coupled to control said line source of radiation, said processor for controlling said line source of radiation to perform a first transmission prescan over said object for a first duration and generating in response thereto a first count density information;
   said processor for computing a second duration for a second transmission scan phase based on said first count density information;
   said processor for controlling said line source of radiation to perform said second transmission scan phase over said object for said second duration and generating in response thereto a second count density information, said second duration representing a minimum duration of exposure of said object required for generating said second count density information;
   said processor for generating a set of attenuation correction factors based on said second count density information, said set of attenuation correction factors for use in correcting image data gathered by said scintillation detector during emission scanning; and a memory unit coupled to store and provide access to said first and said second count density information.

11. An apparatus as described in claim 10 wherein said second count density information is a distribution over different portions of said object and wherein said processor is for inputting a minimum count density wherein said distribution contains at least said minimum count density for each portion of said object.

12. An apparatus as described in claim 11 wherein said processor is for analyzing said first count density information and determining a minimum observed count density in response thereto wherein said minimum observed count density corresponds to a portion of said object that exhibits maximum attenuation.

13. An apparatus as described in claim 12 wherein said processor determines said second duration according to the procedure:

$$Ts = Co \frac{Tp}{Cm}$$

wherein Ts is said second duration, Cm is said minimum observed count density, Tp is said first duration, and Co is said minimum count density.

14. A gamma camera system for collecting transmission data associated with an object, said gamma camera system comprising:

a scintillation detector for receiving radiation and reporting image information;

a line source of radiation for emitting transmission radiation through said object to said scintillation detector;

a gantry structure for positioning said scintillation detector and said line source of radiation;

a computer system for acquiring and processing image information, said computer system coupled to said scintillation detector and coupled to control said line source of radiation, said computer system comprising a processor;

said processor for controlling said line source of radiation to perform a first transmission prescan over said object for a first duration and generating in response thereto a first count density information;

said processor for computing a second duration for a second transmission scan phase based on said first count density information;

said processor for controlling said line source of radiation to perform said second transmission scan phase over said object for said second duration and generating in response thereto a second count density information; and said processor for generating a set of attenuation correction factors based on said second count density information, said set of attenuation correction factors for use in correcting image data gathered during emission scanning.

15. A gamma camera system as described in claim 14 wherein said computer system further comprises a memory unit and wherein said memory unit is coupled to store and provide access to said first and said second count density information.

16. A gamma camera system as described in claim 15 wherein said second count density information is a distribution over different portions of said object and wherein said processor is for inputting a minimum count density wherein said distribution contains at least said minimum count density for each portion of said object.

17. A gamma camera system as described in claim 16 wherein said processor is for analyzing said first count density information and determining a minimum observed count density in response thereto wherein said minimum observed count density corresponds to a portion of said object exhibiting maximum attenuation and wherein said processor determines said second duration according to the procedure:

$$Ts = Co \frac{Tp}{Cm}$$

wherein Ts is said second duration, Cm is said minimum observed count density, Tp is said first duration, and Co is said minimum count density.

18. In a nuclear camera system having a scintillation detector for receiving radiation and reporting image information; a line source of radiation for emitting transmission radiation through an object to said scintillation detector; and a computer system, a computer implemented method of collecting transmission data associated with said object, said method comprising the steps of:

controlling said line source of radiation to perform a first transmission prescan over said object for a first predetermined duration and generating in response thereto a first count density information;

computing a second duration for a second transmission scan phase based on said first count density information; and controlling said line source of radiation to perform said second transmission scan phase over said object for said second duration and generating in response thereto a second count density information.

19. A method as described in claim 18 further comprising the steps of generating a set of attenuation correction factors based on said second count density information, said set of attenuation correction factors for use in correcting image data acquired during emission scanning.

20. A method as described in claim 19 wherein said second count density information is a distribution over different portions of said object and further comprising the step of inputting a minimum count density wherein said distribution contains at least said minimum count density for each portion of said object.

21. A method as described in claim 20 wherein said step of computing a second duration comprises the steps of:

analyzing said first count density information and determining a minimum observed count density in response thereto; and computing said second duration according to the procedure:

$$Ts = Co \frac{Tp}{Cm}$$

wherein Ts is said second duration, Cm is said minimum observed count density value, Tp is said first predetermined duration, and Co is said minimum count density value.

22. A method as described in claim 21 wherein said minimum observed count density corresponds to a portion of said object exhibiting maximum attenuation.

23. In a nuclear camera system having a pair of scintillation detectors for receiving radiation and reporting image information; a pair of radiation line sources each for emitting transmission radiation through an object to an associated scintillation detector; and a computer system, a computer implemented method of collecting transmission data associated with said object, said method comprising the steps of:

obtaining a minimum count density value desired for each portion of a resultant count density distribution;

controlling said pair of radiation line sources to perform a first transmission prescan over said object for a first predetermined duration and generating in response thereto a first count density distribution;

computing a second duration for a second transmission scan phase based on said first count density distribution;

controlling said pair of radiation line sources to perform said second transmission scan phase over said object for said second duration and generating in response thereto said resultant count density distribution, said second duration representing a minimum duration of exposure of said object required to generate said second count density distribution; and generating a set of attenuation correction factors based on said second count density information, said set of attenuation correction factors for use in correcting image data acquired during emission scanning.

24. A method as described in claim 23 wherein said step of computing a second duration comprises the steps of:

analyzing said first count density distribution and determining a minimum observed count density value in response thereto wherein said minimum observed count density value corresponds to a portion of said object exhibiting maximum attenuation; and computing said second duration according to the procedure:

$$Ts = Co \frac{Tp}{Cm}$$

wherein Ts is said second duration, Cm is said minimum observed count density value, Tp is said first predetermined duration, and Co is said minimum count density value.

* * * * *